US 9,146,247 B2

(12) United States Patent
Zahniser et al.

(10) Patent No.: US 9,146,247 B2
(45) Date of Patent: Sep. 29, 2015

(54) SAMPLE APPLICATOR SENSING AND POSITIONING

(75) Inventors: Russell Zahniser, Dorchester, MA (US); David Zahniser, Wellesley, MA (US); Stephen Conroy, Maynard, MA (US); Eric Leknes, Manchester, NH (US); Michael Zahniser, Jamaica Plain, MA (US); Frank L. Pawlowski, Amherst, NH (US)

(73) Assignee: Roche Diagnostics Hematology, Inc., Westborough, MA (US)

( * ) Notice: Subject to any disclaimer, the term of this patent is extended or adjusted under 35 U.S.C. 154(b) by 462 days.

(21) Appl. No.: 13/549,251

(22) Filed: Jul. 13, 2012

(65) Prior Publication Data

US 2013/0021461 A1      Jan. 24, 2013

Related U.S. Application Data

(60) Provisional application No. 61/510,728, filed on Jul. 22, 2011.

(51) Int. Cl.
| | |
|---|---|
| *H04N 7/18* | (2006.01) |
| *G01N 35/00* | (2006.01) |
| *G01N 1/31* | (2006.01) |
| *G01B 11/14* | (2006.01) |
| *G01N 35/10* | (2006.01) |

(52) U.S. Cl.
CPC .......... *G01N 35/00029* (2013.01); *G01B 11/14* (2013.01); *G01N 1/31* (2013.01); *G01N 35/1011* (2013.01)

(58) Field of Classification Search
USPC ........................................................ 348/135
See application file for complete search history.

(56) References Cited

U.S. PATENT DOCUMENTS

| | | | |
|---|---|---|---|
| 4,618,261 | A | 10/1986 | Flanders et al. |
| 5,416,609 | A | 5/1995 | Matsuda et al. |
| 5,437,242 | A | 8/1995 | Hofstetter et al. |
| 5,953,125 | A | 9/1999 | de Groot |
| 6,319,470 | B1 | 11/2001 | Lefevre et al. |
| 7,025,933 | B2 | 4/2006 | Ganz et al. |
| 8,248,590 | B2 | 8/2012 | Pronkine |
| 2004/0131758 | A1 | 7/2004 | Jung et al. |
| 2005/0045653 | A1* | 3/2005 | Tanaka et al. ..................... 222/1 |

(Continued)

OTHER PUBLICATIONS

International Search Report and Written Opinion, mailed Sep. 17, 2012, issued in international application No. PCT/US2012/046784, 14 pgs.

(Continued)

*Primary Examiner* — Tracy Li
(74) *Attorney, Agent, or Firm* — Fish & Richardson P.C.

(57) ABSTRACT

Systems and methods for positioning a sample applicator relative to a substrate include: (a) obtaining an image of the sample applicator in proximity to the substrate, where the image includes a direct image region corresponding to the sample applicator and a first reflected image region corresponding to an image of the sample applicator reflected from a surface of the substrate; (b) determining a position of an edge of the sample applicator in the direct image region; (c) determining a position of a reflected edge of the sample applicator in the first reflected image region; (d) determining a distance between the edge of the sample applicator and the reflected edge of the sample applicator; and (e) determining the position of the sample applicator relative to the substrate based on the distance between the edges.

35 Claims, 7 Drawing Sheets

(56) References Cited

U.S. PATENT DOCUMENTS

| | | | |
|---|---|---|---|
| 2005/0151092 A1 | 7/2005 | Kitagawa | |
| 2005/0212837 A1 | 9/2005 | Nakagawa et al. | |
| 2006/0144331 A1* | 7/2006 | Hanafusa et al. | 118/712 |
| 2008/0210894 A1 | 9/2008 | Ahn et al. | |
| 2009/0269799 A1 | 10/2009 | Winkelman et al. | |
| 2010/0021348 A1* | 1/2010 | Baldassari et al. | 422/99 |
| 2011/0255785 A1* | 10/2011 | Hara et al. | 382/182 |
| 2012/0024416 A1 | 2/2012 | Golias et al. | |

OTHER PUBLICATIONS

International Preliminary Report on Patentability mailed Feb. 6, 2014 in International Application No. PCT/US2012/046784, 9 pgs.
International Search Report and Written Opinion, issued in International Application No. PCT/US2013/050519 on Dec. 9, 2013, 12 pgs.
International Preliminary Report on Patentability, issued in International Application No. PCT/US2013/050519 on Jan. 22, 2015, 6 pgs.
Non-Final Office Action, U.S. Appl. No. 13/942,330, issued on Jan. 29, 2015, 10 pgs.

* cited by examiner

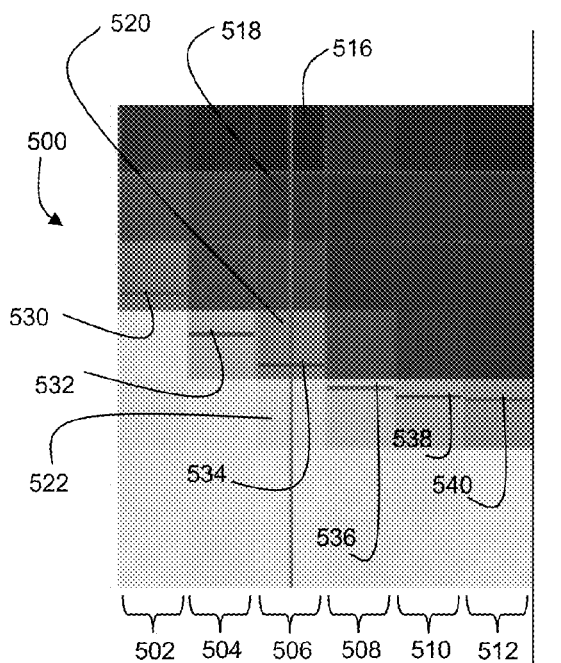
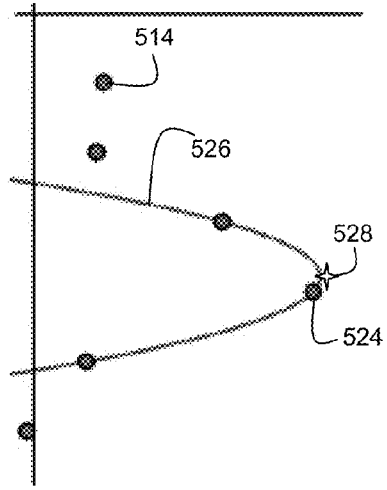
FIG. 5A                FIG. 5B
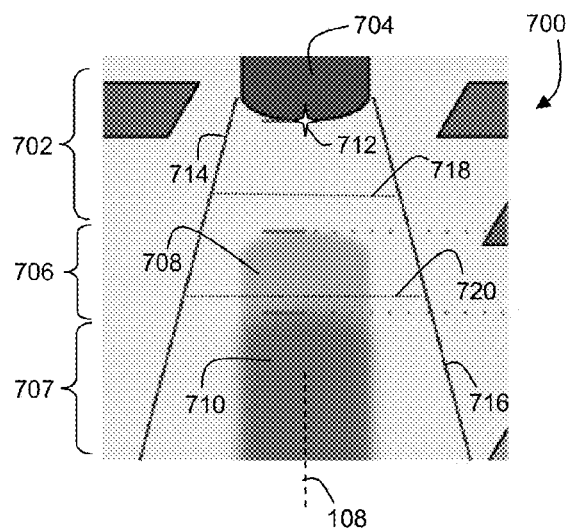
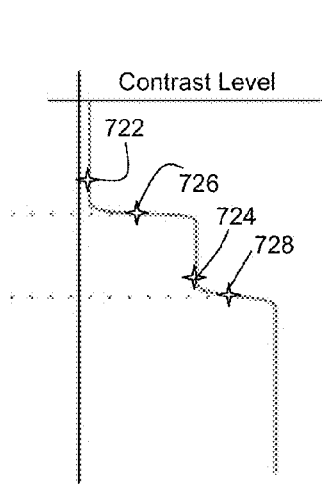
FIG. 7A                FIG. 7B
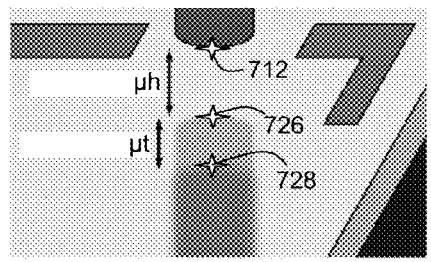
FIG. 7C

SAMPLE APPLICATOR SENSING AND POSITIONING

CROSS-REFERENCE TO RELATED APPLICATIONS

This application claims priority under 35 U.S.C. §119(e) to U.S. Provisional Patent Application No. 61/510,728, filed on Jul. 22, 2011, the entire contents of which are incorporated by reference herein.

TECHNICAL FIELD

This disclosure relates to methods and systems for positioning sample applicators for dispensing a sample onto a substrate.

BACKGROUND

Conventional methods for analyzing biological samples such as blood or body fluids typically include two steps. First, an automated system performs a quantitative analysis of sample characteristics on the sample in a liquid state. For example, a flow cytometer using impedance, fluorescence, and/or scattered light-based measurements processes a sample of blood suspended in a fluid steam to count red blood cells, white blood cells, platelets, and to derive other parameters of a complete blood count. Second, to the extent the flow system detects any abnormalities in the sample (e.g., an abnormally high white blood cell count), the system flags the sample and a laboratory technician reviews the sample manually by examining a dried and stained preparation of the sample on a microscope slide.

To facilitate manual review, the technician typically prepares a "wedge" smear of the blood sample. Smear preparations yield samples with highly variable thicknesses and distribution of blood constituents. The wedge smear often has only a single narrow band with an appropriate cell density for examination and analysis, and the location and shape of this band varies from slide to slide. In addition, due to a lack of uniformity, smear preparations often preclude absolute quantitation of sample properties for a given patient. In general, only relative proportions can be assessed within the smear itself.

A sample preparation method that produces a uniform, high-quality specimen would make visual evaluation of the sample both easier and more accurate. Furthermore, for specimens prepared using a known volume of the sample in a highly consistent manner, it is possible to automate the quantitation of sample properties directly from the specimen, replacing the first step of sample analysis traditionally performed using flow-based systems.

SUMMARY

The systems and methods disclosed herein are used during automated sample preparation in which sample applicators are used to dispense fluid samples onto substrates such as microscope slides. Successfully dispensing fluids to obtain samples of relatively uniform distribution across a substrate depends, in part, on controlling the position of the sample applicator relative to the surface of the substrate that receives the sample. To achieve precise control over the sample applicator, the methods and systems disclosed herein are configured to determine the position of the sample applicator relative to the substrate surface based on one or more images of the applicator, including images reflected from the substrate surface. The image(s) include both a direct image region that corresponds to a direct (e.g., non-reflected) image of the sample applicator above the substrate, and a first reflected image region that corresponds to an image of the sample applicator that is reflected from the substrate surface.

The position of the applicator relative to the substrate surface can be determined based on the distance between the edges of the sample applicator in the direct image region and the first reflected image region. The methods and the systems that implement the methods can be extended to determine the position of the sample applicator at multiple transverse locations relative to the substrate. By initially determining a set of suitable positions of the applicator relative to the substrate surface (e.g., at the corners of the substrate), suitable control signals for producing desired applicator positions can be interpolated at other locations on the substrate surface. In this manner, precise control over the position of the sample applicator relative to the substrate surface can be achieved during dispensing of a fluid sample onto the substrate.

In general, in a first aspect, the disclosure features methods of positioning a sample applicator relative to a substrate, the methods including: (a) obtaining an image of the sample applicator in proximity to the substrate, the image including a direct image region corresponding to the sample applicator and a first reflected image region corresponding to an image of the sample applicator reflected from a surface of the substrate; (b) determining a position of an edge of the sample applicator in the direct image region; (c) determining a position of a reflected edge of the sample applicator in the first reflected image region; (d) determining a distance between the edge of the sample applicator and the reflected edge of the sample applicator; and (e) determining the position of the sample applicator relative to the substrate based on the distance between the edges.

Implementations of the methods can include any one or more of the following features.

Obtaining the image of the sample applicator in proximity to the substrate can include orienting a detector at an angle relative to the surface of the substrate, and recording the image using the detector.

The position of the sample applicator relative to the substrate can include a height of the sample applicator above the surface of the substrate. Determining the height of the sample applicator above the surface of the substrate can include calculating the height based on reference information that includes correlation information relating the distance between the edge of the sample applicator and the reflected edge of the sample applicator to the height.

The methods can include measuring a set of distances between the edge of the sample applicator and the reflected edge of the sample applicator, where measuring each member of the set of distances includes: (a) translating the sample applicator to a new height above the surface of the substrate; (b) obtaining a second image of the sample applicator at the new height in proximity to the substrate, the second image including a direct image region corresponding to the sample applicator and a first reflected image region corresponding to an image of the sample applicator reflected from the surface of the substrate; (c) determining a position of an edge of the sample applicator in the direct image region of the second image; (d) determining a position of a reflected edge of the sample applicator in the first reflected image region of the second image; and (e) determining a distance between the edge of the sample applicator in the direct image region and the reflected edge of the sample applicator in the first reflected image region of the second image.

The methods can include determining a control setting associated with a target position of the sample applicator by interpolating between distances in the measured set of distances. The methods can include storing in a storage unit the control setting and information about a location of the sample applicator relative to the substrate. The set of distances can include at least two distances (e.g., at least ten distances).

The methods can include: (a) translating the sample applicator in a direction perpendicular to a central axis of the applicator to a new location relative to the substrate; (b) measuring a set of distances between the edge of the sample applicator and the reflected edge of the sample applicator; (c) determining a control setting associated with a target position of the sample applicator at the new location; and (d) storing the control setting and information about the new location in the storage unit. The methods can include repeating the steps of translating the sample applicator in a direction perpendicular to the central axis of the sample applicator to a new location relative to the substrate, measuring a set of distances between the edge of the sample applicator and reflected edge of the sample applicator, determining a control setting associated with a target position of the sample applicator at the new location, and storing the control setting and information about the new location in the storage unit, until a number of locations about which information is stored is three or more (e.g., six or more).

The methods can include determining coefficients of an equation of a surface of the substrate. The methods can include determining an orientation of the substrate relative to a plane perpendicular to the central axis of the sample applicator. Determining an orientation of the substrate can include determining a slope of the substrate surface relative to the plane perpendicular to the central axis of the sample applicator.

Determining a position of an edge of the sample applicator in the direct image region can include: (a) selecting columns of pixels in the direct image region that extend in a direction parallel to a central axis of the sample applicator; (b) for each selected column, determining a position of maximum intensity change within the column; (c) determining the position of the edge of the sample applicator based on the positions of maximum intensity change in each selected column of pixels. Determining the position of maximum intensity change within each selected column can include: (a) for each pair of adjacent pixels in the selected column, determining a change in intensity; (b) determining a maximum intensity change between pairs of adjacent pixels in the selected column; and (c) fitting a functional form to the maximum intensity change between pairs of adjacent pixels to determine the position of maximum intensity change within the selected column. Determining the position of the edge of the sample applicator can include fitting the positions of maximum intensity change within each selected column to a functional form. Determining the position of the edge of the sample applicator can include determining an apex point of the sample applicator based on the fitted functional form.

Determining the position of the reflected edge of the sample applicator in the first reflected image region can include: (a) selecting rows of pixels in the first reflected image region that extend in a direction perpendicular to an elongated axis of the sample applicator image; (b) for each selected row, determining an average of an m highest pixel intensities in the row, and determining an average of a k lowest pixel intensities in the row; (c) determining a contrast level associated with the row as a difference between the average of the m highest pixel intensities and the average of the k lowest pixel intensities; and (d) determining the position of the reflected edge of the sample applicator based on the contrast level in each selected row. Determining the position of the reflected edge of the sample applicator based on the contrast level in each selected row can include: (a) identifying a first portion of the first reflected image region based on a contrast level in each selected pixel row, where the first portion does not include the image of the sample applicator; (b) identifying a second portion of the first reflected image region based on a contrast level in each selected pixel row, where the second portion includes the image of the sample applicator; and (c) determining the position of the reflected edge of the sample applicator based on a difference in contrast levels between the first and second portions of the first reflected image region. The quantity m can correspond to at least one fifth of a total number of pixels in each selected row, the quantity k can correspond to at least one fifth of the total number of pixels in each selected row, and there may be no pixels in each selected row that are common to the m pixels and the k pixels.

The surface of the substrate is an upper surface of the substrate closest to the sample applicator. The image of the sample applicator in proximity to the substrate can include a second reflected image region corresponding to an image of the sample applicator reflected from a lower surface of the substrate, and the methods can include: (a) determining a position of a reflected edge of the sample applicator in the second reflected image region; (b) determining a distance between the reflected edges of the sample applicator in the first and second reflected image regions; and (c) determining a thickness of the substrate based on the distance between the reflected edges of the sample applicator in the first and second reflected image regions. Determining the thickness of the substrate can include calculating the thickness based on reference information that includes correlation information relating the distance between the reflected edges of the sample applicator to the thickness.

Determining a position of a reflected edge of the sample applicator in the second reflected image region can include: (a) selecting rows of pixels in the second reflected image region that extend in a direction perpendicular to an elongated axis of the sample applicator image; (b) for each selected row, determining an average of a p highest pixel intensities in the row, and determining an average of a q lowest pixel intensities in the row; (c) determining a contrast level associated with the row as a difference between the average of the p highest pixel intensities and the average of the q lowest pixel intensities; and (d) determining the position of the reflected edge of the sample applicator in the second reflected image region based on a difference between the contrast level in each selected pixel row in the second reflected image region and the contrast level in each selected pixel row in the first reflected image region. The quantity p can correspond to at least one fifth of a total number of pixels in each selected row, the quantity q can correspond to at least one fifth of the total number of pixels in each selected row, and no pixels in each selected row may be common to the p pixels and the q pixels.

The methods can include calibrating the correlation information, where calibrating the correlation information includes determining an offset control signal value that causes an actuator of the sample applicator to provide an upward force that will just be overcome by the force of gravity, storing the offset control signal value, translating the sample applicator toward the substrate until a signal associated with a translation error of the actuator is within an error threshold, and storing the position of the sample applicator when the signal associated with the translation error of the actuator is within the error threshold. Calibrating the correlation information can include setting the height of the sample applicator to zero at the stored position. The methods can include calibrating the correlation information, where calibrating the correlation information includes determining an offset control signal value that causes an actuator of the sample applicator to provide an upward force that will just barely be overcome by the force of gravity (e.g., in some implementations about 0.5, 1, 2, 3, 4, or 5% less than gravity); storing the offset control signal value; lowering the sample applicator slowly until a control signal of the actuator is within an error threshold of the offset control signal; and storing the position of the sample applicator when the control signal of the actuator is within the error threshold of the offset control signal.

Various implementations and embodiments of the methods can also include any one or more of the other features disclosed herein, in any combination, as appropriate.

In another aspect, the disclosure features systems that include a sample applicator, a stage configured to support a substrate, a detector, and an electronic processor, where the system is configured so that when a substrate is supported by the stage: (a) the detector is configured to obtain an image of the sample applicator in proximity to the substrate, the image including a direct image region corresponding to the sample applicator and a first reflected image region corresponding to an image of the sample applicator reflected from a surface of the substrate; and (b) the electronic processor is configured to: (i) determine a position of an edge of the sample applicator in the direct image region; (ii) determine a position of a reflected edge of the sample applicator in the first reflected image region; (iii) determine a distance between the edge of the sample applicator and the reflected edge of the sample applicator; and (iv) determine the position of the sample applicator relative to the substrate based on the distance between the edges.

Various implementations and embodiments of the systems can include any one or more of the following features.

The position of the sample applicator relative to the substrate can include a height of the sample applicator above the surface of the substrate, and the electronic processor can be configured to determine the height of the sample applicator based on reference information that includes correlation information relating the distance between the edge of the sample applicator and the reflected edge of the sample applicator to the height.

The electronic processor can be configured to measure a set of distances between the edge of the sample applicator and the reflected edge of the sample applicator by: (a) translating the sample applicator to a new height above the surface of the substrate; (b) obtaining a second image of the sample applicator at the new height in proximity to the substrate, the second image including a direct image region corresponding to the sample applicator and a first reflected image region corresponding to an image of the sample applicator reflected from the surface of the substrate; (c) determining a position of an edge of the sample applicator in the direct image region of the second image; (d) determining a position of a reflected edge of the sample applicator in the first reflected image region of the second image; and (e) determining a distance between the edge of the sample applicator in the direct image region and the reflected edge of the sample applicator in the first reflected image region of the second image.

The electronic processor can be configured to determine a control setting associated with a target position of the sample applicator by interpolating between distances in the measured set of distances. The system can include a storage unit connected to the electronic processor, where the electronic processor is configured to store the control setting and information about a location of the sample applicator relative to the substrate in the storage unit.

The electronic processor can be configured to: (a) translate the sample applicator in a direction perpendicular to a central axis of the sample applicator to a new location relative to the substrate; (b) measure a set of distances between the edge of the sample applicator and the reflected edge of the sample applicator; (c) determine a control setting associated with the target position of the sample applicator at the new location; and (d) store the control setting and information about the new location in the storage unit. The electronic processor can be configured to determine coefficients of an equation of a plane corresponding to a surface of the substrate based on the stored control settings. The electronic processor can be configured to determine an orientation of the substrate relative to a plane perpendicular to the central axis of the sample applicator based on the stored control settings.

Implementations and embodiments of the system can also include any one or more of the other features disclosed herein, in any combination, as appropriate.

As used herein, the term "sample applicator" refers to a device that dispenses a sample onto a substrate. Typically, although not always, sample applicators include a fluid conduit for dispensing fluid samples. Sample applicators can include pipettes, needles, and tubes, for example.

A "sample" is a solution, a suspension, a liquid, or another type of fluid sample dispensed by the sample applicator onto a surface of the substrate. A sample can be a biological specimen such as blood, for example.

A "substrate" is a member onto which a sample can be dispensed. Typically, but not always, substrates have a planar receiving surface onto which the sample can be dispensed by the sample applicator. An example substrate is a microscope slide, or any other reflective material capable of supporting a sample.

The "upper surface" of the substrate corresponds to the substrate surface closest to the sample applicator. The "lower surface" of the substrate corresponds to the substrate surface opposite to the upper surface.

A "direct image region" corresponds to a region in an image that includes a direct image of the sample applicator. A direct image is an image that has not been reflected from a surface of the substrate. A "first reflected image region" is a region, typically from the same image, that includes an image of the sample applicator that has been reflected from a surface of the substrate (either the upper surface or the lower surface). A "second reflected image region" is a region, typically from the same image, that includes an image of the sample applicator that has also been reflected from a surface of the substrate. In some embodiments, the first and second reflected image regions correspond to images of the sample applicator that have been reflected from different surfaces of the substrate (e.g., the upper and lower surfaces, respectively).

An "edge of the sample applicator" refers to a boundary, in the direct image region, that demarcates the sample applicator from other features in the direct image region. A "reflected edge of the sample applicator" refers to a boundary, in the first reflected image region, that demarcates the reflected image of the sample applicator from other features in the first reflected image region.

When comparing the intensities I(1) and I(2) of pixels 1 and 2, respectively, in a given image region, the "change in intensity" corresponds to I(2)-I(1). Typically, the sample applicator in an image region appears as a dark feature against a brighter background (e.g., the background is of higher intensity). Accordingly, the change in intensity will be positive when pixel 2 is a background pixel and pixel 1 corresponds to the sample applicator.

The quantity "contrast level" is a measure of the intensity variability among a set of pixels. Contrast level can be calculated as follows: first, by selecting from the pixel set a first subset of pixels with the highest intensities among the pixels in the set, and a second subset with the lowest intensities among pixels in the set; and second, by calculating the difference between the average intensities for the two subsets. The subsets can be a fixed number of pixels or proportional to the size of the pixel set (e.g., ⅕ of the pixels in the set). For example, the average intensity for the subset of pixels with the highest intensities can correspond to the average of the n largest pixel intensities for a particular row of pixels in an image. The average intensity for the subset of pixels with the lowest intensities can correspond to the average of the m smallest pixel intensities for the particular row. The values of n and m can be different, or the same. For example, n can have a value of 10, but can range from 1 through the total number of pixels for the row. In addition, m can have a value of 10, but can range from 1 through the total number of pixels for the row. Typically, the values of n and m are selected for the set of pixels so that none of the pixels selected is common to both the first and second subsets.

The "height" of the sample applicator refers to the minimum distance between the upper surface of the substrate and the portion of the sample applicator nearest to the upper surface. For an applicator with an extended central axis (e.g., a pipette or tube) oriented perpendicular to the substrate surface, the height is measured along a direction parallel to the central axis. For an applicator without an extended central axis or a central axis that is not oriented perpendicular to the substrate surface, the height is measured in a direction parallel to a surface normal of the substrate surface.

The "location" of the sample applicator relative to the substrate corresponds to the applicator's two-dimensional displacement, in a plane parallel to the upper surface of the substrate, relative to a reference position on the substrate surface.

The "thickness" of the substrate corresponds to a maximum dimension of the substrate measured between the upper and lower surfaces in a direction perpendicular to the plane of the upper surface.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

FIG. 5A is a schematic representative direct image of a sample applicator showing locations of maximum intensity change in each column of pixels.

FIG. 5B is a graph showing change in intensity plotted as a function of position for a column of pixels in the image of FIG. 5A.

FIG. 7A is a schematic representative reflected image of a sample applicator.

FIG. 7B is a graph showing contrast level plotted as a function of row position for each row of pixels in the image of FIG. 7A.

FIG. 7C is a schematic representative image of a sample applicator showing apex positions of the sample applicator.

Like reference symbols in the various drawings indicate like elements.

DETAILED DESCRIPTION

Figure 1A:
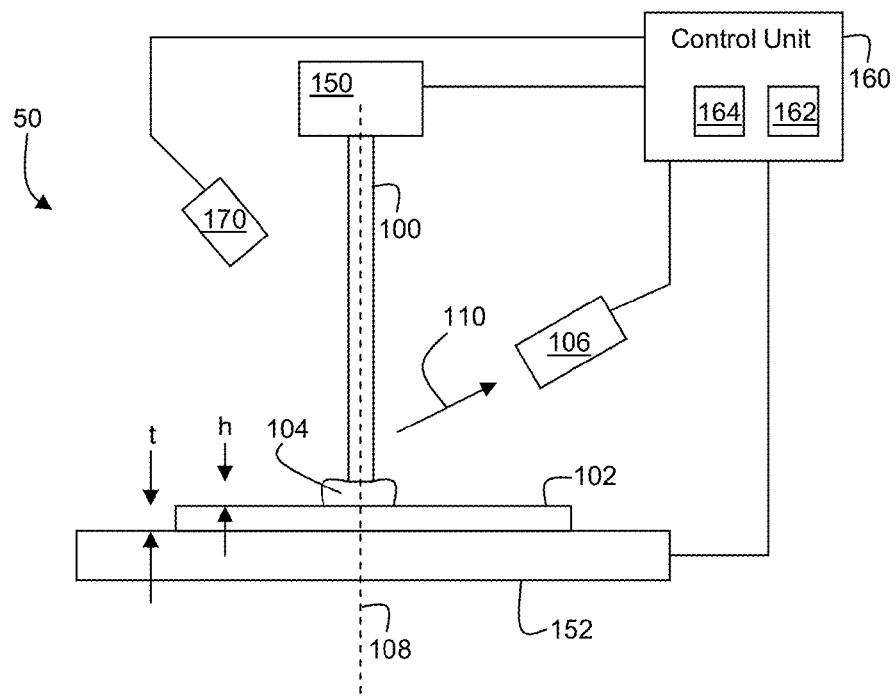
FIG. 1A is a schematic diagram showing a side view of a sample applicator positioned perpendicular to an upper surface of a substrate.

To accurately quantify results directly from a prepared sample on a substrate, the composition, configuration, and height or thickness of the deposited sample should be as highly uniform as possible across the substrate surface so that each analyzed sub-area of the sample is representative of the sample prepared on the substrate as a whole as well, and of the patient from whom the sample was extracted. In addition, highly consistent and uniformly prepared samples provide a basis to directly compare samples and analysis results across multiple patients. By preparing samples in a uniform manner, automated methods can be used for analysis, significantly improving throughput.

A variety of different methods can be used to prepare samples in automated fashion for subsequent analysis. To improve uniformity, a known quantity of a fluid sample (e.g., liquids, suspensions, solutions, and other mixtures such as human or animal blood or bodily fluids, with or without diluent, e.g., cells from bone marrow, urine, vaginal tissue, epithelial tissue, tumors, semen, spittle, and other body fluids) can be dispensed onto a substrate surface in a controlled manner to ensure that fluid does not build up or spread too thinly at particular locations on the substrate surface (e.g., to achieve, as closely as possible, uniformity in the sample deposited on the substrate). By way of example, the following discussion refers to the dispersal and analysis of blood samples on microscope slides. However, the methods and systems disclosed herein can be applied to the preparation and analysis of a wide variety of fluid samples, as described above, on a wide variety of substrates. Substrates can include, but are not limited to, glass or plastic microscope slides, polished or mirrored ceramic slides, polished metal substrates, plastic or other flexible specimen films, and/or any other reflective materials capable of supporting a sample.

Sample Application Systems and Methods

The methods and systems disclosed herein can be used with automated sample preparation systems that dispense a known quantity of blood onto the surface of a microscope slide using a sample applicator. Typically, the applicator moves in relation to the surface of the slide, continuously dispensing blood while moving relative to the slide. The blood can be dispensed in a variety of patterns according to the movement of the sample applicator. In some embodiments, for example, a stage holding the substrate moves the slide in a raster pattern under the sample applicator, which results in a continuous "painting" of rows of blood on the substrate surface. In certain embodiments, the applicator or stage can move in a spiral or boustrophedon pattern with each successively painted row next to the previous row painted in the opposite direction across the sample surface. By way of example, the following discussion refers to dispensing blood in a boustrophedon pattern on the substrate surface. However, more generally, the methods and systems disclosed herein can be applied to dispense fluids in a wide variety of patterns including, but not limited to, raster patterns and spiral patterns as either or both of the sample applicator or the stage supporting the substrate move during the sample deposition process.

In some embodiments, when blood is dispensed in a boustrophedon pattern, the sample applicator—positioned at a certain height above the substrate surface—sweeps across the sample surface in successive rows, dispensing a continuous volume of blood as it moves. As the rows of blood dry on the substrate surface, they coalesce to form a continuous film of blood. The uniformity of the film depends on the manner in which the rows of blood are dispensed onto the substrate. The rate at which the blood is dispensed and the spacings or overlap between successive rows of blood are chosen so that adjacent rows of blood, when they spread laterally and merge, form a film with a cellular distribution across the substrate that is as uniform as possible, e.g., one cell in thickness. Ideally, the cells within the film are deposited at a desired thickness on the substrate as densely as possible while maintaining consistent spacing between cells to minimize overlap or contact between adjacent cells (e.g., a layer of cells uniformly distributed across the surface of the substrate where each cell is separated from adjacent cells by half of the cell's thickness).

An important factor that influences the uniformity of the overall film is the uniformity of the width of the individual rows of blood deposited on a substrate. Typically, the greater the uniformity of the width of each row, the greater the uniformity of the overall film that is formed on the substrate. The width of a given row of dispensed blood is related to the height of the applicator above the substrate upper surface as the applicator is translated to new locations relative to the surface because of capillary forces within sample on the substrate contiguous with the sample being dispensed from the applicator. To achieve a uniform film with a monolayer of cells on the surface of the substrate, the capillary forces within the sample are balanced against the dispersive forces that tend to cause spreading of the dispensed rows on the substrate surface. By balancing these forces, adjacent rows merge to form a uniform film on the sample surface in which the cells and other sample constituents are dispersed neither too thinly nor too irregularly.

In addition to controlling the width of a dispensed row of blood by controlling the height of the applicator above the substrate, the viscosity of the fluid sample and the rate of speed at which the applicator and substrate are moving with respect to each other influence the width of a given row of blood dispensed onto the substrate. In general, the greater the height of the applicator above the surface (e.g., the larger the gap between the applicator and the surface), the greater the width of the dispensed rows. That is, the rate at which blood is dispensed onto the surface of the slide is related to the volume of the region between the applicator and the substrate surface. Variations in the volume of this region are therefore related to variations in height of the applicator above the substrate surface. Thus, to dispense rows that are as nearly uniform in width, height, and cellular distribution as possible, it is important: (a) to maintain as uniform a height of the applicator above the substrate surface as possible as the applicator is translated or moved from location to location relative to the substrate surface; and (b) to dispense the sample at a flow rate that neither succumbs to the capillary forces present in the sample deposited on the substrate and contiguous with the sample in the applicator, nor overpowers these capillary forces. In addition, depositing slightly overlapping rows (e.g., overlapping by $1/8$, $1/4$, $1/2$, or $1/3$ of the sample applicator diameter) can improve the overall uniformity of a sample deposited on a substrate.

Because the viscosity and surface tension of blood are both relatively high, the amount of lateral spreading of the dispensed rows is smaller than would occur for rows of a fluid with smaller surface tension, such as water or a sample of blood mixed with a diluent. Thus, the viscosity and surface tension can be determined and monitored to ensure that the spacing between rows of blood is suitable to achieve the desired overall coverage.

It has been determined through careful experimentation that for a sample applicator having an outer diameter of about 1500 to 500 microns and an inner diameter of about 500 to 100 microns (e.g., a sample applicator with an outer diameter of about 812 microns and an inner diameter of about 431 microns), used to dispense rows of blood that cover an area of 600 square millimeters on the surface of a glass substrate, a suitable height for the applicator above the surface of the substrate (e.g., a microscope slide) is about 8 to 20 microns (e.g., 10, 12, 14, 16, or 18 microns). On average, for example, the height of the sample applicator above the surface of the glass substrate can be maintained at about 12 microns. At this height, to ensure that rows of blood are dispensed with sufficient uniformity, the height of the applicator above the substrate surface should vary by no more than 2 microns.

In addition, it has been observed that ordinary microscope slides can vary in thickness from slide to slide by as much as 25 microns between the upper and lower slide surfaces. The variation in microscope slide thicknesses can significantly alter the consistency or uniformity of samples deposited on a slide if the applicator is fixed in position in a laboratory frame of reference, without regard to the thickness of the substrate. If the thickness of the substrate varies, then maintaining the applicator at a fixed position along an axis normal to the substrate surface may result in variations in the height of the applicator above the substrate surface as the applicator and substrate move relative to one another due to the varying thickness of the substrate. Further, although substrates such as microscope slides are maintained in an orientation such that the surface of the slide is planar and nominally orthogonal to a central axis of the applicator, in practice, a substrate can be oriented such that its upper surface is angled somewhat with respect to the central axis of the applicator, further complicating the task of maintaining a constant applicator height.

Given the above constraints, methods and systems that can determine the height of the sample applicator above the upper surface of the substrate are important for ensuring that automated methods can be used to prepare blood samples that correspond to a consistent volume of analyte (e.g., 1 microliter of blood) dispersed in a sample uniformly distributed across the surface of a substrate. Further, because of the relatively small tolerance for variations in the applicator height, it is important that the applicator height be determined without allowing the applicator to physically contact the substrate during sample deposition or outside a calibration process. Uncontrolled or unintended physical contact between the applicator and the substrate could potentially damage the applicator tip or displace the substrate from its original position, precluding an accurate determination of the applicator position. In addition, if the applicator tip includes a drop of sample and the drop contacts the substrate before the applicator deposits the sample onto the substrate, additional cells may be deposited onto the substrate surface, thereby erroneously affecting the quantitative results for a sample of expected volume.

The methods and systems disclosed herein can be used to determine both the height of the sample applicator above the substrate surface and the thickness of the substrate. Typically, height measurements are performed at one or more substrate surface locations. At each location, the sample applicator is scanned through a series of displacements relative to the substrate surface. At each displacement value, the height of the applicator above the substrate surface is determined, and correlated with a particular setting of the applicator manipulator that controls displacement of the applicator. At each location, a manipulator setting is determined that corresponds to the targeted height (e.g., 8, 10, 12, 14, 16, 18, or 20 microns) of the applicator above the substrate surface. In this manner, suitable positions for the applicator are determined at multiple locations on the substrate surface. At each location, the thickness of the substrate can also be determined to further refine the positional height data for the applicator.

After this information has been determined for the substrate, the applicator can dispense rows of blood without making any further measurements of the applicator height. In effect, the initial set of height measurements used to determine suitable settings for the applicator manipulator functions as calibration data for the dispensing operation. By calibrating prior to the dispensing operation, a known quantity of blood can be dispensed continuously (e.g., in rows) without performing applicator height measurements, while enabling a continuous, controlled height adjustment of the applicator to ensure that the blood is dispensed regularly and uniformly, and each row is allowed to dry for the same amount of time before an adjacent row is dispensed. This pattern of regular, uniform row dispensing helps to ensure that the resulting blood sample is as uniform as possible when it has dried.

Sample Applicator Height Determination Systems and Methods

FIG. 1A shows a schematic diagram of a system 50 that features a sample applicator 100 positioned above an upper surface of a substrate 102. Sample applicator 100 dispenses a fluid sample 104 onto substrate 102. Substrate 102 has a thickness t, and sample applicator 100 is positioned at a height h above the upper surface of substrate 102. Both t and h are measured along a direction parallel to the central axis 108 of sample applicator 100. A detector 106 is positioned to detect light rays 110 from sample applicator 100 and/or substrate 102 that propagate at an angle to central axis 108 of sample applicator 100. Sample applicator 100 is mechanically connected to a manipulator 150, and substrate 102 is supported by a stage 152. Manipulator 150 and stage 152 are electrically (e.g., by wires or wirelessly) connected to control unit 160, which includes an electronic processor 162.

Figure 1B:
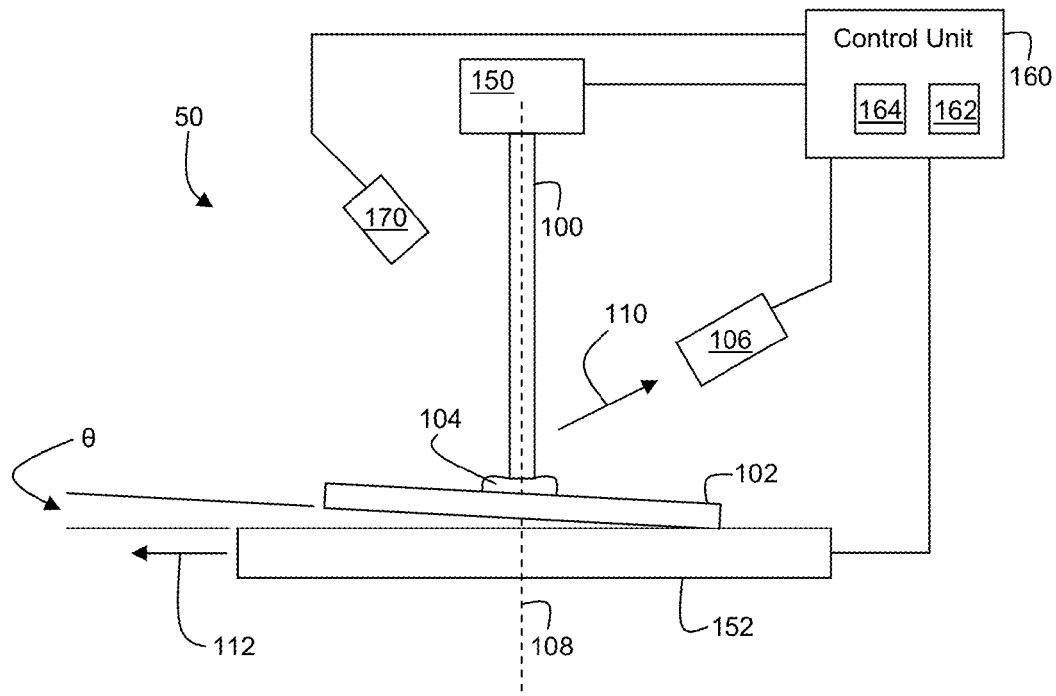
FIG. 1B is a schematic diagram showing a side view of a sample applicator positioned at an angle with respect to an upper surface of a substrate.

In FIG. 1A, the central axis 108 of sample applicator 100 is nominally orthogonal to the plane of substrate 102. In certain embodiments, the central axis of sample applicator 100 may not be orthogonal to the plane of substrate 102. FIG. 1B shows a schematic diagram of a sample applicator 100 that dispenses fluid 104 onto the surface of substrate 102. In FIG. 1B, substrate 102 is oriented at an angle θ with respect to a plane perpendicular to central axis 108 of sample applicator 100. The angle θ corresponds to the tilt angle of substrate 102 in an external coordinate system, such as the coordinate system of manipulator 150. In FIG. 1B, axis 112 corresponds to a direction along which sample applicator 102 is translated by manipulator 150. Manipulator 150 can also translate sample applicator 102 along a second axis orthogonal to the plane of FIG. 1B and to axis 112; substrate 102 can be un-tilted with respect to the second axis (e.g., as in FIG. 1A), or substrate 102 can be tilted with respect to the second axis. In general, the tilt angle with respect to the second axis can be the same as, or different from, the tilt angle with respect to axis 112.

Figure 2:
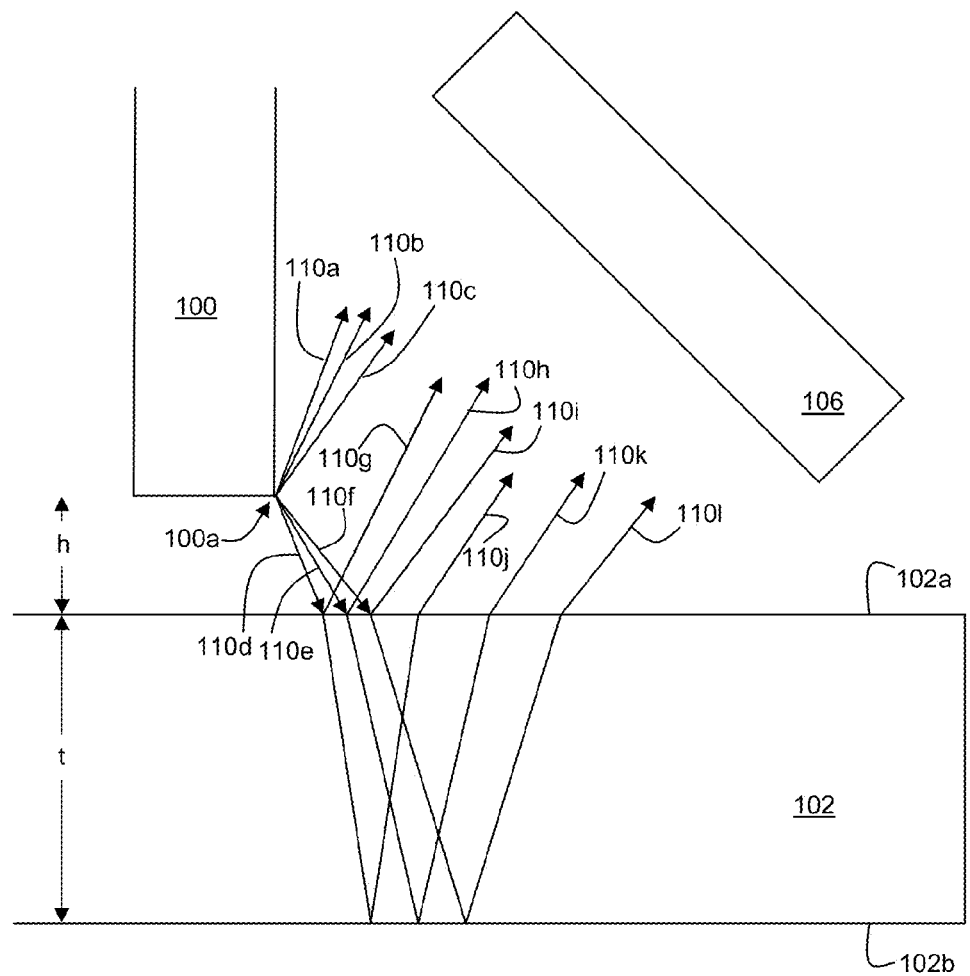
FIG. 2 is a schematic diagram showing a side view of a sample applicator positioned relative to a substrate and a detector that captures a direct and a reflected image of the sample applicator.

FIG. 2 shows an enlarged view of the embodiment of FIG. 1A. In FIG. 2 (as in FIG. 1A), a sample applicator 100 is positioned at a height h above an upper surface of substrate 102. Fluid 104—dispensed by applicator 100—is not shown in FIG. 2 for clarity. Light rays emerging from multiple points on sample applicator 100 are captured by detector 106. By way of illustration, a series of light rays are shown emerging from point 100a on the surface of sample applicator 100. Rays 110a, 110b, and 110c emerge from point 100a and are detected directly by detector 106; these rays form a direct (e.g., unreflected) image of point 100a. In an image formed on detector 106, rays 110a-c form a portion of a direct image region that corresponds to the direct image of applicator 100.

Rays 110d, 110e, and 110f also emerge from point 100a. However, rays 100d-f initially propagate downwards toward upper surface 102a of substrate 102. Upon encountering upper surface 102a, a portion of each of rays 110d-f is reflected from the upper surface toward detector 106. The reflected portions correspond to rays 110g, 110h, and 110i. These rays form an indirect (e.g., reflected) image of point 100a in a first reflected image region of the image formed on detector 106.

Portions of rays 110d-f in FIG. 2 undergo refraction rather than reflection at upper surface 102a. These refracted rays propagate through substrate 102, and are reflected from lower surface 102b of substrate 102. Upon encountering upper surface 102a a second time, the rays again undergo refraction at the upper surface, emerge from substrate 102, and propagate toward detector 106 as rays 110j, 110k, and 110l. Rays 110j-l form a second indirect (e.g., reflected) image of point 100a in a second reflected image region of the image formed on detector 106.

Figure 3:
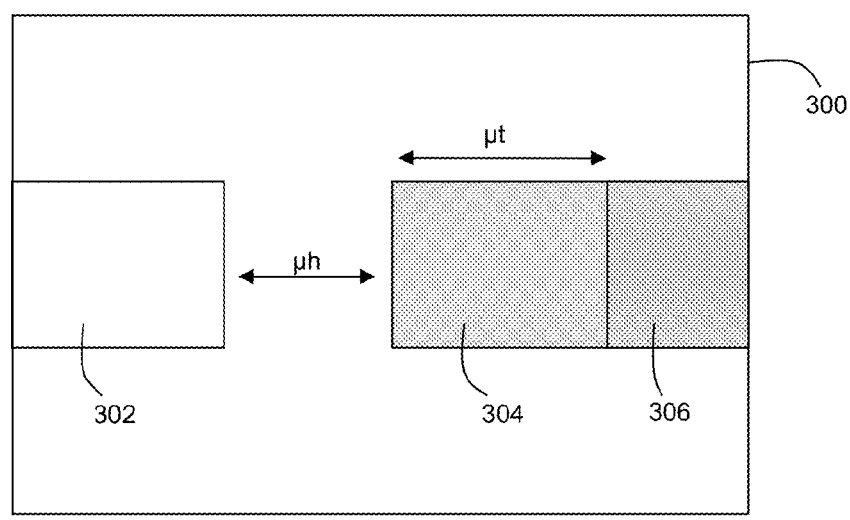
FIG. 3 is a schematic representative image showing a direct image of a sample applicator within a direct image region and two reflected images of the sample applicator within reflected image regions.

FIG. 3 shows a schematic, exemplary image 300 formed on detector 106. Image 300 includes a direct image 302 of sample applicator 100, a first reflected image 304 of sample applicator 100, and a second reflected image 306 of sample applicator 100. First reflected image 304 is formed by rays reflected from upper surface 102a of substrate 102 (e.g., rays 110g-i). Second reflected image 306 is formed by rays reflected from lower surface 102b of substrate 102 (e.g., rays 110j-l).

As is evident from FIGS. 2 and 3, the direct image corresponding to rays 110a-c is displaced laterally from the reflected image corresponding to the bundle of rays 110g-i in the plane of the image formed on detector 106 by an amount μh that is related to the height h of sample applicator 100 above surface 102a of substrate 102. As sample applicator 100 is moved closer to upper surface 102a, the displacement μh between the direct and reflected images of sample applicator 100 is reduced. Conversely, as h increases, the image displacement μh also increases.

In similar fashion, the reflected image corresponding to rays 110g-i is displaced laterally from the reflected image corresponding to rays 110j-l in the image plane on detector 106 by an amount μt that is related to the thickness t of substrate 102. For thicker substrates (e.g., where the distance between surfaces 102a and 102b is larger), the displacement μt is also larger. For thinner substrates, μt is reduced.

Accordingly, by determining displacements between the direct and reflected images of sample applicator 100 in one or more images captured by detector 106, the height h of sample applicator above substrate 102 and the thickness t of substrate 102 can be estimated. Further, by calibrating image pixel measurements with known linear displacements, pixel-based measurements of height and thickness can be converted into length units (e.g., microns).

Figure 4:
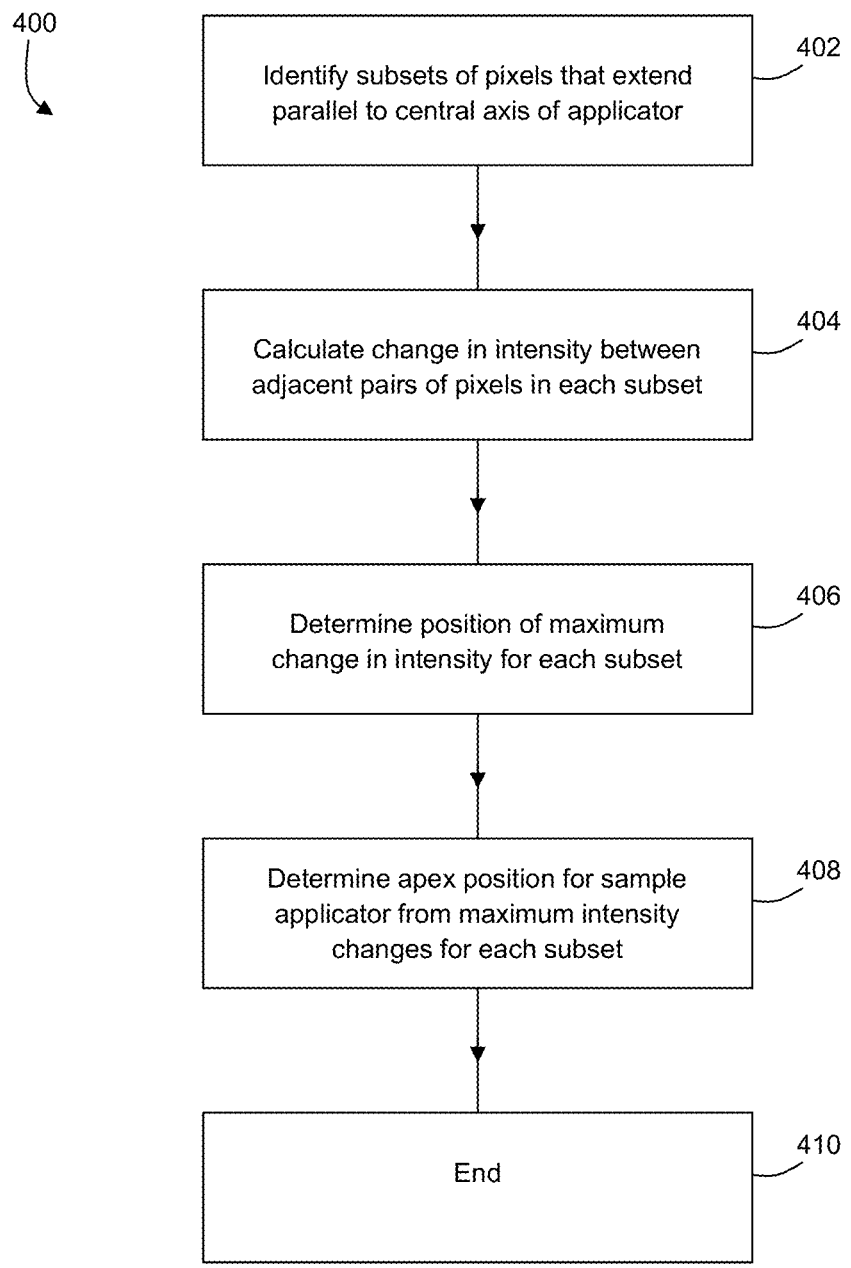
FIG. 4 is a flow chart that includes a series of steps for determining an apex position of a direct image of a sample applicator.

To determine the position of sample applicator 100 relative to substrate 102 (e.g., the height of sample applicator 100 above substrate 102), the displacement μh between images 302 and 304 in FIG. 3 is determined. The first step in measuring this distance is to determine an apex position for the direct image 302 of sample applicator 100. FIG. 4 is a flow chart 400 that includes a series of steps for determining an apex position of a direct image of a sample applicator. In a first step 402 in flow chart 400, a direct image of sample applicator 100 is analyzed to select pixel subsets that will be used to calculate an intensity gradient along the central axis 108 of the applicator. FIG. 5A shows a half-image 500 of a sample applicator 100. The central axis 108 of the applicator shown in the half-image is coincident with the right-most edge of image 500. In FIG. 5A, pixel columns 502, 504, 506, 508, 510, and 512 extend parallel to central axis 108. Accordingly, each of these pixel columns is selected in step 402 for further analysis.

Next, in step 404, each subset (e.g., column) of pixels identified in step 402 is separately analyzed by calculating an intensity gradient along the column. In certain embodiments, the gradient is calculated along the pixel column using an edge detection kernel (e.g., a four-pixel kernel of [1, 3, −3, −1]). In some embodiments, the gradient can be calculated by determining the intensity differences between each adjacent pixel in the column. The change in intensity ΔI between any two adjacent pixels 1 and 2 is calculated as ΔI=I(2)−I(1), where I(1) and I(2) are the measured intensities of pixels 1 and 2, respectively. This procedure is illustrated in FIG. 5B for pixel column 506, where the change in intensity is plotted along the upper (horizontal) axis against column position on the left-hand (vertical) axis. For example, the uppermost plotted point 514 along the vertical axis corresponds to the change in intensity between the first pixel 516 and the second pixel 518 in column 506. The vertical coordinate of point 514 corresponds to the dividing line between the pixels; the horizontal coordinate of point 514 corresponds to the calculated change in intensity between the pixels. As the intensity of second pixel 518 in column 506 is greater than the intensity of first pixel 516 (e.g., the second pixel appears brighter than the first), the change in intensity is positive. As is evident from FIG. 5B, the largest change in intensity in column 506 occurs between fourth pixel 520 and fifth pixel 522; this change in intensity is represented by point 524 in FIG. 5B.

Returning to FIG. 4, in step 406, the position of the maximum change in intensity is determined for each pixel column. For each pixel column, the process of determining the position of the maximum change in intensity is generally accomplished by fitting a functional form to the change in intensity values calculated between adjacent pixels of the column in step 404. This process is illustrated in FIG. 5B, where curve 526 has been fitted to some of the calculated change in intensity values. In general, a variety of different functional forms can be used to determine the position of the maximum change in intensity. In FIG. 5B, a parabolic functional form was fitted to the maximum change in intensity between adjacent pixels (e.g., point 524) and to the calculated change in intensity values on either side of the maximum. As shown in FIG. 5B, the position of maximum change in intensity for pixel column 506 was then interpolated as the peak of the fitted parabolic curve, point 528. In the example of FIG. 5B, the position of the maximum change in intensity, point 528, did not correspond exactly with the positions of any of the divisions between adjacent pixels. Instead, the position of maximum intensity change fell within pixel 520.

This procedure is repeated for each of the pixel columns in FIG. 5A to determine a position of maximum intensity change for each column. The determined maximal positions are shown as lines 530, 532, 534, 536, 538, and 540 in FIG. 5A. As can be seen from comparing FIGS. 5A and 5B, the maximum position 534 in column 506 corresponds to the position of point 528 in FIG. 5B.

Returning to FIG. 4, after the positions of maximum intensity change for each pixel column have been determined in step 406, the apex position of the sample applicator is determined in step 408. In general, the apex position of the sample applicator corresponds approximately to the maximum change in intensity that is furthest from the dark edge among the pixel columns of image 500 in FIG. 5A (i.e., the top horizontal row of pixels shown in FIG. 5A). Referring to FIG. 5A, this dark edge of the sample applicator image corresponds to the body of the sample applicator, while the bright edge corresponds to the end of the applicator that is nearest to substrate 102. Accordingly, the apex position of sample applicator 100—the point on the direct image of the sample applicator that is nearest to the reflected images of the sample applicator—is identified approximately as the position of the maximum change in intensity, selected from among all of the pixel columns, that is nearest to the bright edge of the direct image. In FIG. 5A, the position of maximum change in intensity for pixel column 512, position 540, is closest to the bright edge of image 500 (i.e., the bottom horizontal row of pixels shown in FIG. 5A). Accordingly, the apex position of the sample applicator in the direct image of the applicator is approximately identified as point 540 in FIG. 5A.

In some embodiments, the apex position of the sample applicator can be further refined by fitting a functional form to the positions of maximum change in intensity for each pixel column. For example, a functional form (e.g., a parabolic functional form) can be fitted to positions 530, 532, 534, 536, 538, and 540, and the apex of the sample applicator can be determined as the vertex of the fitted parabolic form. In FIG. 5A, a parabola fitted to positions 530, 532, 534, 536, 538, and 540 will have a vertex that is approximately coincident with position 540. More generally, however, the fitted functional form may not be exactly coincident with the any of the positions of maximum change in intensity for the pixel columns, due to imaging artifacts and irregularities in the shape of sample applicator 100, for example.

It has been experimentally determined that a parabolic functional form typically yields an accurate apex position for the sample applicator. As discussed above, the apex position of applicator 100 can be determined from the direct image as the maximal point of the fitted function (e.g., the apex of the parabola) closest to the substrate. Other functional forms can also be used to determine the apex position for the sample applicator. For example, in some embodiments, an elliptical functional form can be fitted to the applicator edge locations to determine the apex position of the sample applicator. Typically, an elliptical functional form matches the edges of the applicator closely because the edge profile of the applicator is elliptical in reflected images.

Having determined the apex position of the sample applicator in the direct image using at least one of the foregoing methods, the process shown in FIG. 4 terminates at step 410.

Figure 6:
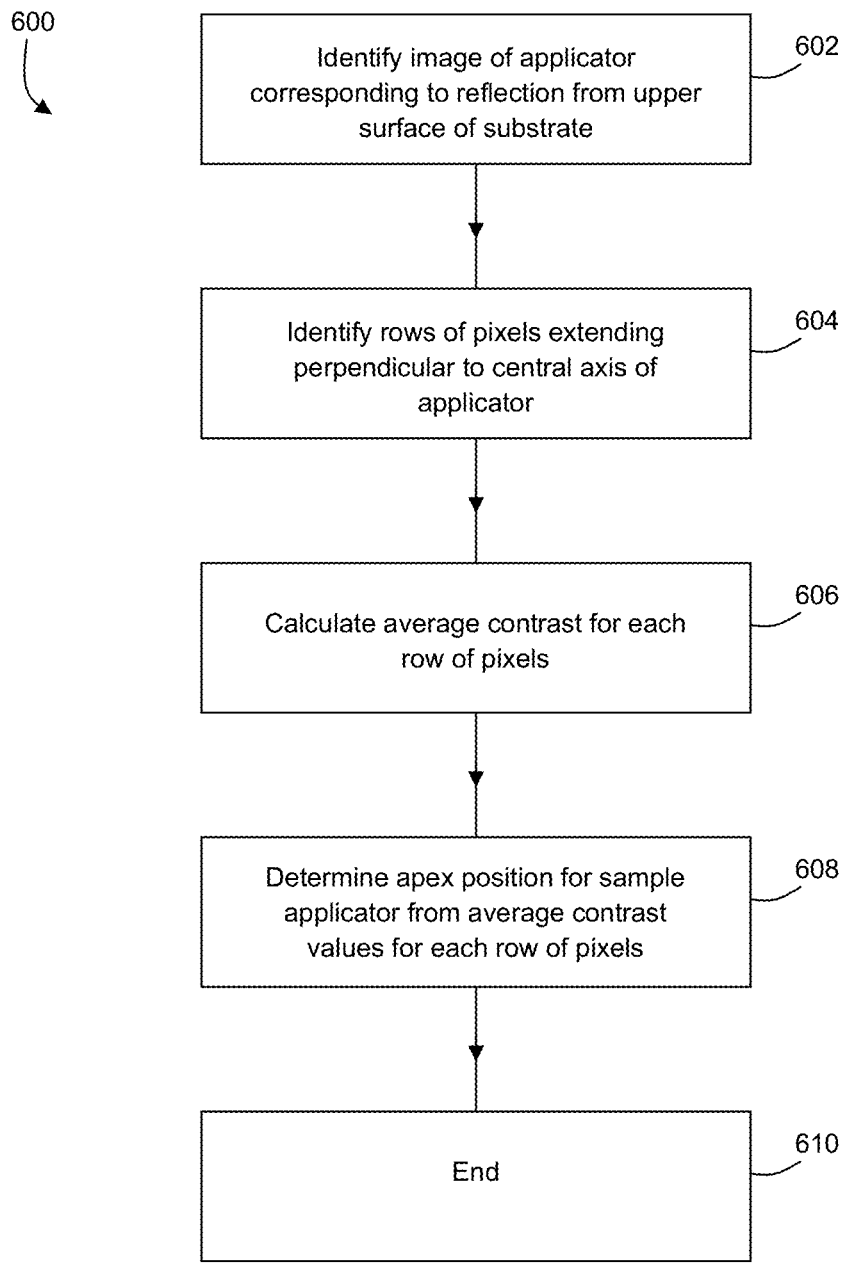
FIG. 6 is a flow chart that includes a series of steps for determining an apex position of a reflected image of a sample applicator.

The next step in determining the position of sample applicator 100 relative to substrate 102 is to determine an apex position for the image of sample applicator 100 that corresponds to the reflection from upper surface 102a of substrate 102. FIG. 6 shows a flow chart 600 that includes a series of steps for determining an apex position of a reflected image of the sample applicator. The first step 602 in flow chart 600 is to identify the image of the sample applicator that corresponds to the reflection from upper surface 102a of substrate 102.

In some embodiments, the procedure disclosed previously in connection with FIG. 4 for locating the apex of the direct image of the sample applicator can be used to determine the apex position of a reflected image of the sample applicator. Alternatively, and particularly when the reflected image of the sample applicator is not as well focused as the direct image, other procedures can be used to determine the apex position. FIG. 7A shows a schematic representation of a typical image 700 captured by detector 106. A direct image region 702 of image 700 includes a direct image 704 of sample applicator 100. A first reflected image region 706 includes a first reflected image 708 of sample applicator 100. A second reflected image region 707 includes a second reflected image 710 (overlaid on a portion of the first reflected image) of sample applicator 100. First reflected image 708 corresponds to reflection from upper surface 102a of substrate 102, as explained above.

Returning to FIG. 6, the second step 604 in flow chart 600 is to identify rows of pixels that extend in a direction perpendicular to the central axis 108 of sample applicator 100 in the reflected image region. In FIG. 7A, the central axis 108 in the first and second reflected image regions extends in a direction parallel to the left- and right-hand edges of image 700; accordingly, suitable rows of pixels extend in a direction parallel to the top and bottom edges of image 700.

The identification of suitable rows of pixels to be used in finding the apex position of the reflected image of the sample applicator can also involve excluding certain rows from consideration. For example, the apex position of the direct image of the sample applicator, point 712, has already been determined using the procedure described in flow chart 400. Accordingly, with reference to image 700, pixel rows above point 712 need not be further considered, as the reflected image of the sample applicator will not appear in these rows.

In certain embodiments, pixel rows can also be foreshortened to speed up computational operations. For example, referring to FIG. 7A, the edge positions of the direct image of the sample applicator can be determined from the analysis of image 704. The edge positions of the reflected images 708 and 710 of the sample applicator can be assumed to fall in approximately the same locations as the edge positions of the direct image 704. Accordingly, pixel rows that are used to find the apex position of the reflected image of the sample applicator can be shortened by applying edge boundaries 714 and 716 in FIG. 7A. Further, edge boundaries can be selected to exclude other substrate features (e.g., painted logos, specimen frames, fiducial marks) from the first reflected image region. Edge boundaries 714 and 716 can be angled with respect to central axis 108 as shown in FIG. 7A, or can be parallel to central axis 108. The angle of the edge boundaries with respect to central axis 108 can be 5° or more (e.g., 10° or more, 15° or more, 20° or more, 25° or more, 30° or more, 40° or more, 50° or more).

Returning again to FIG. 6, after suitable rows of pixels have been identified in step 604 (which can include foreshortening the identified rows), the contrast level for each row of pixels is determined in step 606. The contrast level can be determined in a variety of ways; the following discussion presents a particular series of steps for performing this calculation, but it is to be understood that other methods can also be used for measuring the variability in intensity for each row of pixels.

In certain embodiments, the first step in determining the contrast level for a particular row of pixels includes determining an average intensity for a subset of the brightest (e.g., highest intensity) pixels within a given row. The determination of an average intensity for a subset of pixels with the highest intensity values for a pixel row involves determining the average of the n largest intensities of pixels in the row. The value of n can be 1 or more (e.g., 2 or more, 3 or more, 4 or more, 5 or more, 6 or more, 8 or more, 10 or more, 15 or more, 20 or more, 30 or more), or n can be expressed as a fraction of the total number of pixels in the row (e.g., ¼ or less, ⅕ or less, ⅙ or less, ⅐ or less). Typically, the value of n is chosen so that the subset of highest intensity pixels does not include pixels that correspond to the reflected image 708 of the sample applicator.

The next step in determining the contrast level for the pixel row is to determine the average intensity for a subset of the darkest (e.g., lowest intensity) pixels within the row. The average intensity for the darkest pixels with a row can be calculated as the average of the m smallest intensities for pixels in the row. The value of m can be 1 or more (e.g., 2 or more, 3 or more, 4 or more, 5 or more, 6 or more, 8 or more, 10 or more, 15 or more, 20 or more, 30 or more), or m can be expressed as a fraction of the total number of pixels in the row (e.g., ¼ or less, ⅕ or less, ⅙ or less, ⅐ or less). Typically, the value of m is chosen so that the subset of lowest intensity pixels does not include pixels that correspond to the background portion of the image (i.e., that does not contain the reflected image 708 of the sample applicator).

Finally, the contrast level for the pixel row is calculated as the difference between the average intensity for the subset of highest intensity pixels for the row, and the average intensity for the subset of lowest intensity pixels for the row. The foregoing process can be repeated for each row of pixels identified in step 604, so that each pixel row has an associated contrast level.

Then, in step 608, the apex position of the reflected image of sample applicator 100 can be determined based on the change in contrast level values between each of the pixel rows. FIG. 7B shows contrast level (on the upper horizontal axis) plotted as a function of pixel row (on the left-hand vertical axis) for image 700 in FIG. 7A. Determination of the apex position of the reflected image of the sample applicator is based on the observation that in pixel rows that do not correspond to an image of the sample applicator, the contrast level will be relatively small, and in pixel rows that do correspond to an image of the sample applicator, the contrast level will be considerably larger. For example, in FIG. 7A, pixel row 718 does not correspond to first reflected image 708 of the sample applicator; as a result, the contrast level in row 718 is small, as indicated by point 722 in FIG. 7B. In contrast, pixel row 720 does correspond to first reflected image 708; accordingly, the contrast level in row 720 is larger than in row 718, as indicated by point 724 in FIG. 7B.

By plotting the contrast level as a function of pixel row in FIG. 7B, pixel rows that correspond to no reflected images, to the first reflected image 708, and to the combination of the first and second reflected images, 708 and 710, can be identified based on the changes in contrast level between pixel rows. As shown in FIGS. 7A and 7B, the applicator tip in the first reflected image region of FIG. 7A corresponds to the largest change in contrast level between pixel rows in first reflected image region 706, indicated as point 726 in FIG. 7B. With the apex position of the first reflected image 708 of the sample applicator determined in step 608, the process in flow chart 600 then terminates at step 610. A similar process can be repeated, as further described below, to determine the apex position of second reflected image 710 of the sample applicator, shown as point 728 in FIG. 7B.

Determining Applicator Height

Having determined the apex positions of direct image 704 and of first reflected image 708 from the substrate's upper surface as described above, the height of sample applicator 100 relative to substrate 102 can be determined by calculating the separation h between the apex positions. FIG. 7C shows a schematic representative image in which the apex position of the direct image, point 712, and the apex position of the first reflected image, point 726, have been determined. The separation $\mu h$ between the images can be calculated in straightforward fashion (in image pixel units) from the difference between the apex positions. If desired, the separation $\mu h$ can be converted to length units (e.g., microns) based on previously determined calibration information.

Calibration—General Considerations

The calibration information can be determined by correlating a known separation (in length units such as microns) between the sample applicator and the upper surface of a substrate based on a known position of the stage or applicator to a pixel separation between the applicator and the upper surface of the substrate in a reflected image region. Thereafter, the calibration information can be used to interpolate pixel separations and positions of the stage or applicator to find the desired position of the stage or applicator that provides the desired pixel separation, and the position of the stage or applicator can be offset based on the calibrated separation to achieve the desired separation between the applicator and the upper surface of the slide. Alternatively, control unit 160 can (a) correlate manipulator 150 or stage 152 positions to instances when detector 106 acquires an image of the sample applicator contacting a substrate, and (b) extrapolate the correlated manipulator or stage positions to a desired separation between the sample applicator and substrate.

Surface Touch Detection Calibration

A variety of methods can be used to calibrate the systems disclosed herein so that measurements of the separation $\mu h$ between direct and reflected images of the sample applicator can be converted to measurements of the height h of the sample applicator above the surface of substrate 102. One such method is discussed below, but it is to be understood that other methods can also be used for calibration.

In some embodiments, the actuators used to control the position of the sample applicator (e.g., actuators present in manipulator 150 and/or stage 152 and controlled by control unit 160) can include non-screw driven linear actuators, such as linear crossed roller bearings or air-bearing linear actuators, such as those available from Dover (Westborough, Mass.), in which motor, bearing, and encoder are not in direct contact. In addition to permitting movement along an axis when a suitable control signal is delivered, such actuators can also permit generation and measurement of force along the direction of motion. When such actuators are used in the systems disclosed herein, obtaining calibration information typically occurs according to a two-step procedure separated into a first "Digital to Analog Converters ("DAC") calibration" step and a second "applicator displacement" step.

In the DAC calibration step, with the sample applicator not in contact with the surface of the slide, the servo loop that typically drives the actuator is terminated and the actuator's amplifier is immediately re-enabled with a fixed DAC offset control signal. This DAC offset signal is delivered to the actuator by manipulator 150 from control unit 160 to initiate motion of the actuator in an "upward" direction (e.g., parallel to central axis 108 of the applicator and away from the surface of substrate 102). As a result, the actuator and sample applicator are together driven upwards by the fixed DAC offset control signal. After allowing the fixed DAC offset control signal to move the actuator and sample applicator for a set period of time, the actuator position is measured. The calibration routine begins again with a smaller DAC offset control signal, and continues to repeat until movement of the actuator, during the set time period, passes a predetermined threshold condition in the downward direction. The DAC offset control signal value that satisfies this threshold is stored. The value of the stored DAC offset control signal, when applied without an active servo loop, produces sufficient upward force such that the actuator will just barely be overcome by the force of gravity.

Once the DAC offset control signal has been calibrated, the actuator moves the sample applicator to a position that is known to be above the surface of the substrate. A fatal following error threshold is established (e.g., entry by a system operator, retrieval from a storage medium, or hard-coded into software or hardware) such that when the servo loop following error exceeds the fatal following error, the servo loop is terminated. The actuator and sample applicator are slowly displaced towards the surface of the substrate, under control of the servo loop, while the servo loop following error is measured by control unit 160. When the sample applicator makes physical contact with the surface of the substrate and continues to drive downward, the servo loop following error builds up and quickly exceeds the fatal following error; the servo loop is then terminated. Control unit 160 then re-enables the actuator's amplifier and activates the calibrated DAC offset control signal.

The result of this second stage of calibration is that the sample applicator comes to rest nearly weightlessly on the surface of the substrate. After waiting for a period of time for actuator to settle into position, control unit 160 reads the position of the actuator and optionally converts the position into position units (e.g., microns). This value is stored as the position of the surface of the substrate (e.g., the h=0 position). The sample applicator can then be translated to a position above the surface of the substrate, and the position (e.g., measured by reading from the actuator's encoder) can be correlated with a pixel separation as disclosed above.

Such measurements can be repeated as many times as desired to produce accurate calibration information. It has been found that calibration information produced in this manner is repeatable to better than 500 nm, and contact between the sample applicator and the substrate introduces no more than 1 micron of deflection to the substrate. Additional features and aspects of using air bearing actuators for calibration are disclosed, for example, in a document entitled "Force Generation and Measurement," by Kevin McCarthy, published in Drives & Controls (March 2002), and available from Dover Motion on the Internet at "dovermotion.com" under "WhitePapersPage.aspx," the entire contents of which are incorporated herein by reference. Further, while servo motors can be used with manipulator 150 or stage 152 to implement the surface touch detection calibration technique, other types of motors (e.g., stepper motors) can be used to accomplish the technique.

By way of example, the foregoing surface touch detection calibration procedure can be performed at initialization of an automated sample preparation system, at predetermined times during normal operation or maintenance of such system, or upon receipt of a system error message relating to the quality of a prepared sample on a substrate (e.g., a low magnification or high magnification imaging station cannot accurately identify or count one or more constituents within a sample).

Determining Substrate Thickness

The methods and systems disclosed herein can also be used to determine the thickness of the substrate, e.g., a microscope slide, by comparing apex positions of the images reflected from the upper and lower surfaces of a transparent substrate.

The process disclosed above in flow chart 600 can also be used to determine an apex position of the image of the sample applicator that is reflected from lower surface 102b of substrate 102 (i.e., the second reflected image 710 in the second reflected image region 707). As shown in FIG. 7B, for example, just as there is a significant difference between the contrast level for pixel rows that correspond to no reflected image and pixel rows that correspond to first reflected image 708, there is typically also a significant difference between the contrast level for pixel rows that correspond to the overlap of first reflected image 708 and second reflected image 710, and pixel rows that correspond only to first reflected image 708. The apex position for second reflected image 710 is indicated as point 728 in FIGS. 7B and 7C.

With reference to FIG. 7C, the separation between apex positions 726 and 728, $\mu t$, can then be calculated to provide an indication of the thickness of substrate 102. As disclosed above in connection with the separation $\mu h$, the value of $\mu t$—determined in pixel units from the image in FIG. 7C—can be converted to linear units using suitable calibration information, which can be obtained in a manner similar to the procedure described above, or in a variety of other ways, including performing a series of calibration runs with substrates of known thickness to assemble a calibration table of measured values of $\mu t$ and the corresponding known thicknesses t. During subsequent operation of the systems disclosed herein, a thickness t corresponding to a measured value of $\mu t$ can be interpolated from the values in the calibration table.

Selecting an Appropriate Applicator Height to Dispense a Desired Sample Distribution In the foregoing description, sample applicator 100 is positioned at a fixed height h above the upper surface 102a of substrate 102 while the separation $\mu h$ is determined from an image such as that shown in FIG. 7C. Sample applicator 100 can be mechanically connected to a manipulator that controls translation of sample manipulator 100 in three coordinate dimensions. In the embodiment shown in FIG. 1A, for example, sample applicator 100 is connected to manipulator 150. Associated with manipulator 150 is a coordinate system that corresponds to axes along which sample applicator 100 can be translated. For example, sample applicator 100 can be translated along a z-coordinate direction of manipulator 150, which extends parallel to central axis 108 of sample applicator 100—to vary the height h of the sample applicator above upper surface 102a of substrate 102. Further, sample applicator 100 can be translated along x- and y-coordinate directions, each of which is perpendicular to the z-coordinate direction. The x- and y-coordinate directions are each parallel to a plane oriented perpendicular to central axis 108. When the tilt angle θ of substrate 102 is zero, the x- and y-coordinate directions are also parallel to the plane formed by substrate 102; translating sample applicator 100 in either or both of the x- and y-coordinate directions therefore positions the sample applicator at a new location relative to substrate 102, but does not change the height h of sample applicator 100 relative to substrate 102.

Alternatively, in some embodiments, stage 152 can be used to translate substrate 102 in the x-, y, and z-coordinate directions relative to sample applicator 102. Further, in certain embodiments, both stage 152 and manipulator 150 can be used to translate sample applicator 100 relative to substrate 102, with motion in the in x-, y, and z-coordinate directions apportioned between stage 152 and manipulator 150. In the following disclosure, adjustment of the sample applicator's height via manipulator 150 is discussed; however, it should be understood that the methods disclosed can also be implemented via adjustment of the height of sample applicator 100 using stage 152 alone, or by using stage 152 in combination with manipulator 150.

In the methods disclosed above for determining the separation $\mu h$, sample applicator 100 remains at both a fixed height and a fixed location relative to substrate 102. However, as discussed above, careful experimentation has determined suitable heights for dispensing certain fluids onto certain substrates. In particular, it has been determined that for dispensing blood onto microscope slides to form a film that is approximately one-cell thick, sample applicator 100 should be maintained at a height of about 12 microns above the surface of the slide. This height value was determined for a specific rate of sample dispensing (e.g., translation speed of sample applicator 100 relative to substrate 102) and for a specific sample viscosity. More generally, sample applicator 100 should be maintained at a height of between 8 microns and 20 microns above the surface of the slide (e.g., at a height of about 8 microns, about 10 microns, about 12 microns, about 14 microns, about 16 microns, or about 18 microns, or within a range of 10 to 14, 16, or 18 microns) when dispensing blood onto microscope slides.

In general, the following factors influence the ability to dispense a sample uniformly on a substrate at an even distribution, and therefore have an effect on the appropriate height of the sample applicator above the surface of the substrate:

(1) the flow rate of the sample dispensed from the applicator should equal the desired volume of sample to be dispensed during the sample dispensing period;

(2) as the sample applicator translation speed relative to the substrate increases, the applicator height above the substrate should decrease proportionally (although the proportionality relationship may not be linear, and the applicator height should not decrease below a minimum height below which damage occurs to cells);

(3) as the sample viscosity increases relative to the surface tension of the sample dispensed onto the substrate, the applicator height above the surface of the substrate should decrease to prevent disruptions or "tears" in the sample flow as it is deposited on the substrate;

(4) as the substrate wettability increases, the sample applicator height above the substrate should decrease to maintain under the applicator a constant volume of sample being dispensed onto the substrate; and (5) as the sample applicator inner diameter increases, the applicator height above the substrate should decrease (although not below the minimum height below which damage occurs to cells) to maintain under the applicator a constant volume of sample being dispensed onto the substrate.

In some embodiments, to ensure that sample applicator 100 is positioned at a suitable height above substrate 102 when fluid 104 is later dispensed onto the substrate, sample applicator 100 is maintained at a specific location relative to substrate 102 (e.g., at a particular x- and y-coordinate position in the coordinate system of the manipulator), and the height of sample applicator 100 above substrate 102 is varied (e.g., sample applicator 100 is translated along the z-coordinate direction in the coordinate system of manipulator 150). At each new height setting of the manipulator, the steps disclosed above in flow charts 400 and 600 are repeated to determine the separation μh.

Then, using calibration information that relates the measured image separation μh to the actual height h of sample applicator 100 above substrate 102 and/or to particular control settings of manipulator 150, a suitable control setting for the manipulator is selected to yield a sample applicator height that corresponds to the desired target applicator height at a particular location of sample applicator 100 relative to substrate 102.

This procedure is illustrated with reference to FIG. 8, which shows a calibration curve 800 that relates control settings $V_i$ of manipulator 150 (or stage 152) to a series of measured image separations μh. To generate the points shown in FIG. 8, sample applicator 100 was positioned at a series of six different heights above upper surface 102a of substrate 102 by applying six different control settings to manipulator 150 (or stage 152) using control unit 160. The location of sample applicator 100 in the x-y plane relative to substrate 102 was the same for each different height (along the z axis). At each different height, an image was obtained by detector 106 showing both a direct image of sample applicator 100 and a reflected image of sample applicator 100. The separation between the direct and reflected images, μh, was determined. The six measured image separations, $\mu h_1$-$\mu h_6$, are plotted on the vertical axis of FIG. 8 as a function of the six different control settings $V_1$-$V_6$ applied to manipulator 150 (or stage 152) to position sample applicator 100 at the six different heights.

It is known from previously determined calibration information that target separation $\mu h_t$ corresponds to the desired target height $h_t$ of sample applicator 100 above substrate 102. For example, for dispensing a blood sample onto a microscope slide, previous calibration steps have determined that a target sample applicator height $h_t$ above the surface of substrate 102 (e.g., 12 microns) corresponds to a particular z coordinate position of manipulator 150 (or stage 152). As shown in FIG. 8, target separation $\mu h_t$ falls in between measured separations $\mu h_3$ and $\mu h_4$, which correspond to manipulator (or stage) control settings $V_3$ and $V_4$, respectively.

To determine the manipulator (or stage) control setting that yields the target sample applicator height $h_t$ (e.g., 12 microns), interpolation between the measured points (V,μh) can be used. In particular, interpolation between points ($V_3$, $\mu h_3$) and ($V_4$,$\mu h_4$) can be used to determine the control setting $V_t$ that yields the target separation $\mu h_t$. Because the target separation $\mu h_t$ corresponds to the target applicator height $h_t$, control setting $V_t$ applied to manipulator 150 (or stage 152) yields the desired target sample applicator height $h_t$.

Figure 8:
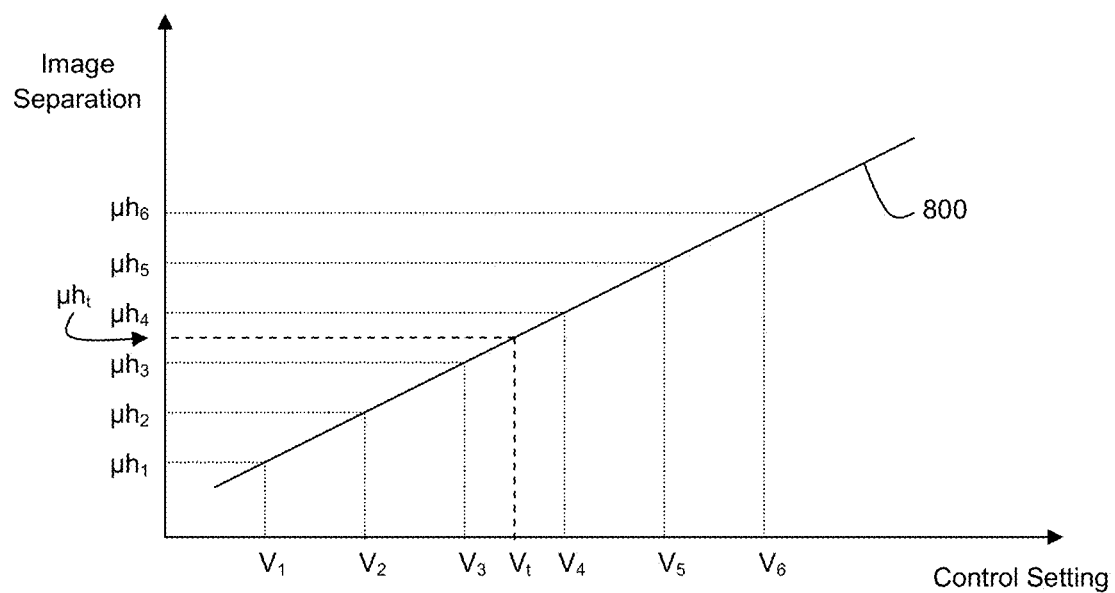
FIG. 8 is a schematic graph showing image separation plotted as a function of a manipulator control setting.

Although a total of six different manipulator (or stage) settings were used in FIG. 8 to determine target control setting $V_t$, more generally, any number of manipulator (or stage) height settings can be used. For example, the number of sample applicator height settings (which is the same as the number of manipulator or stage control settings) can be 2 or more (e.g., 3 or more, 4 or more, 6 or more, 8 or more, 10 or more, 15 or more, 20 or more).

Figure 9:
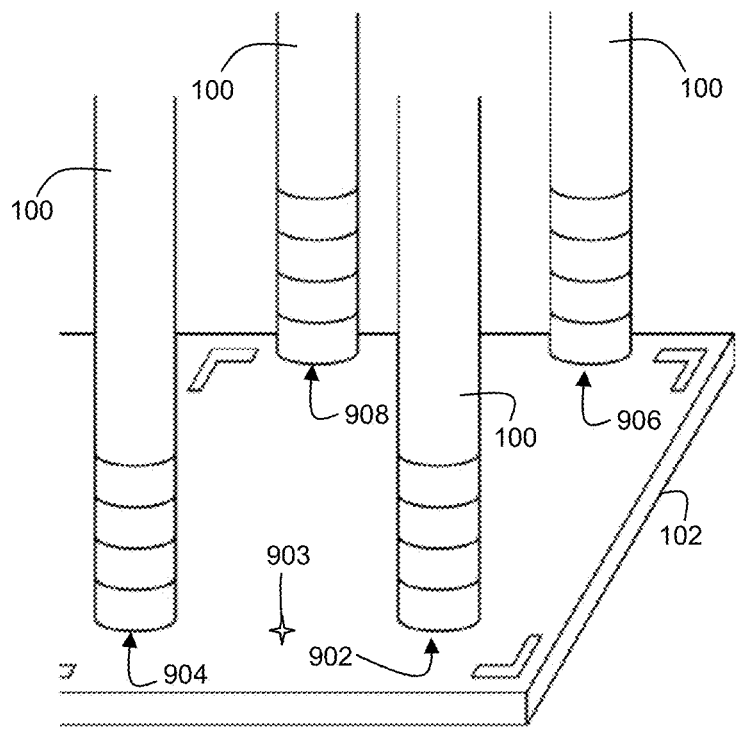
FIG. 9 is a schematic diagram of a substrate showing the determination of a control setting associated with the sample applicator at a plurality of locations relative to the upper surface of the substrate.

For a particular location of sample applicator 100 relative to substrate 102, the process disclosed herein yields a control setting $V_t$ of the manipulator (or stage) that will ensure that sample applicator 100 is positioned at a desired height above upper surface 102a of substrate 102 at that location. As shown in FIG. 9, the process disclosed above can be repeated for multiple different locations 902, 904, 906, and 908 of sample applicator 100 relative to substrate 102. At each location, the height of sample applicator above substrate 102 can be varied by translating manipulator 150 (or stage 152) along the z-coordinate axis of the manipulator by applying different control settings to the manipulator (or stage). The measured image separations μh at the different heights can be used to determine a target control setting $V_t$ of the manipulator (or stage) that will ensure that sample applicator 100 is positioned at a desired height above substrate 102 at that location.

Suitable control settings can be determined at any number of locations of sample applicator 100 relative to substrate 102. In FIG. 9, suitable control settings are determined at four different locations. More generally, however, the number of locations can be one or more (e.g., two or more, three or more, four or more, six or more, eight or more, ten or more, 15 or more, 20 or more, or 30 or more).

After suitable control settings have been determined at a fixed number of locations, suitable control settings can be estimated at other locations by using, e.g., interpolation techniques. For example, referring to FIG. 9, suitable control settings $V_t$ are determined at locations 902 and 904. A suitable control setting $V_t$ that yields a sample applicator height of, e.g., 10 microns, above substrate 102 can be estimated at location 903 by interpolating between the control settings determined at locations 902 and 904.

The thickness of substrate 102 can also be measured at any of locations 902, 904, 906, and 908 using the steps disclosed above in connection with flow chart 600. In particular, the separation μt between the two reflected images of sample applicator 100 need only be determined once at each location; this separation does not change as sample applicator 100 is translated along the z-coordinate axis of manipulator 150 (or stage 152). Accordingly, μt can be determined at a single height. The image separation μt can be converted to yield a thickness t measured in linear units (e.g., microns) using calibration information if desired.

With suitable control settings for the manipulator (or stage) determined at specific locations of sample applicator 100 relative to substrate 102, manipulator 150 (or stage 152) can be positioned such that sample applicator 100 is positioned at any location relative to substrate 102, and the height of the sample applicator above the substrate's upper surface can be maintained at a desired value. Thus, fluid 104 can be dispensed from nearly a constant height above substrate 102, ensuring that rows of the dispensed fluid are as nearly uniform as possible. In this manner, the samples produced are of greater uniformity than those produced using, e.g., manual methods.

Determining Substrate Orientation

In some embodiments, the orientation of substrate 102 can be determined. With reference to FIG. 1B, determining the orientation of substrate 102 can include determining the tilt angle θ between the plane defined by substrate 102 and a plane orthogonal to central axis 108 of sample applicator 100. Determining the orientation of substrate 102 can also include determining parameters associated with an equation f(x,y) that describes upper surface 102a of substrate 102 as a function of position in the (x,y) coordinate plane of manipulator 150 (or stage 152). In general, the orientation of a plane can be determined when three points on the plane are known. Accordingly, when the number of stored control settings (which typically corresponds to the number of distinct locations of sample applicator 100 relative to substrate 102 at which control settings are determined) is three or more, the equation of the plane describing surface 102a can be determined directly from the stored control settings. In some embodiments, the stored control settings are first converted to displacement values expressed in linear units (e.g., microns) using calibration information, and then the displacement values are used to determine the coefficients of the equation of the plane of surface 102a. It has been observed that as a result of the slope of the plane of substrate 102 supported by stage 152, the vertical coordinate of surface 102a of the substrate (in the coordinate system of manipulator 150 or stage 152) can vary by as much as 30 microns between (x,y) locations on opposite ends of the substrate. The equation of the plane that describes surface 102a can also be used, for example, to determine the tilt angle of surface 102a. Additionally, with four or more stored control settings, it is possible to track non-planar surface substrates such as a slightly curved substrate by fitting a more complex equation f(x,y) describing a curved surface to the values of the control settings. Methods for determining an equation of a plane describing or relative to a surface are found in co-pending U.S. patent application Ser. No. 13/019,118, filed on Feb. 1, 2011, the entire contents of which are incorporated herein by reference.

System Components

Returning again to FIG. 1A, manipulator 150 can include a variety of different devices. In general, manipulator 150 functions to translate sample applicator 100 in three different, orthogonal coordinate directions. Suitable manipulators include, for example, actuators activated by step-and-repeat motors, and piezoelectric actuators.

Detector 106 can include a variety of devices for capturing images of sample applicator 100. In some embodiments, for example, detector 106 can include a CCD array detector. In certain embodiments, detector 106 can include a CMOS-based array detector. Detector 106 can also include other optical imaging elements such as filters, lenses, beam splitters, and dispersive optical elements.

Stage 152 is configured to support substrate 102 during dispensing of fluid 104. In certain embodiments, stage 152 is formed of a rigid material such as a metal (e.g., aluminum and/or stainless steel) and/or a plastic material (e.g., a Teflon®-based material). Stage 152 can also include actuators for translating substrate 102 (and part or all of stage 152) in one or more coordinate directions, e.g., in the x-y plane, while applicator 100 remains stationary to dispense the sample fluid. In some embodiments, stage 152 can include actuators for changing an orientation of substrate 102 and part or all of stage 152. Control unit 160 is connected to stage 152 and can issue control signals to stage 152 to initiate translation and/or re-orientation of substrate 102.

In some embodiments, system 50 can include a light source 170 for directing incident light onto sample applicator 100. Light source 170 can be electrically connected to control unit 160 as shown in FIG. 1A. Light source 170 can include, for example, one or more incandescent, fluorescent, diode-based, and/or laser sources. Incident light produced by light source 170 can include wavelengths in one or more of the ultraviolet, visible, and infrared regions of the electromagnetic spectrum.

Control unit 160 includes electronic processor 162, which can be configured to control various components in system 50 and perform any of the method steps disclosed herein. For example, electronic processor 162 can be configured to direct detector 106 to capture one or more images of sample applicator 100 as described herein. Further, electronic processor 162 can be configured to direct light source 170 to emit incident light that illuminates sample applicator 100 during image capture.

Electronic processor 162 can be further configured to transmit control signals to manipulator 150 to cause manipulator 150 to translate sample applicator 100 and/or stage 152 as disclosed herein. In particular, control signals from electronic processor 162 can direct manipulator 150 to translate sample applicator 100 along the x- and/or y-coordinate directions of manipulator 150 to a new location relative to substrate 102. Alternatively or in addition, electronic processor 162 can transmit control signals to stage 152 to translate substrate 102 in the x- and/or y direction, while the applicator 100 remains stationary. Electronic processor 162 can also transmit control signals that direct manipulator 150 to translate sample applicator 100 along the z-coordinate direction of manipulator 150 to a new height above substrate 102, and can transmit control signals to stage 152 to translate substrate 102 (e.g., while sample applicator 100 remains stationary) to change the height of applicator 100 above substrate 102.

In some embodiments, control unit 160 includes a storage unit 164. Storage unit 164 can include, for example, one or more of a variety of different devices for storing information optically, electrically, and/or magnetically. Exemplary devices include, but are not limited to, magnetic storage devices such as hard drives and floppy disks, optical storage devices such as CD and/or DVD drives and their storage media, and electronic devices such as flash memory devices and solid state drives. Storage unit 164 can be configured to store any of the values or quantities disclosed herein, including the locations of sample applicator 100 relative to substrate 102, control settings determined for the sample applicator that ensure the applicator is maintained at a constant height above the upper surface 102a of substrate 102, the measured heights of the sample applicator above substrate 102, the separations μh and/or μt between images, the measured thicknesses of substrate 102, and software containing instructions that, when executed, cause processor 162 to perform any one or more of the functions or steps disclosed herein.

Automated Sample Preparation Systems

The systems and methods disclosed herein can be used with a variety of different automated sample preparation systems. Exemplary systems are disclosed, for example, in U.S. patent application Ser. No. 13/293,050, filed on Nov. 9, 2011, and now published as U.S. Patent Application Publication No. US 2012/0149050, the entire contents of which are incorporated herein by reference.

Figure 10:
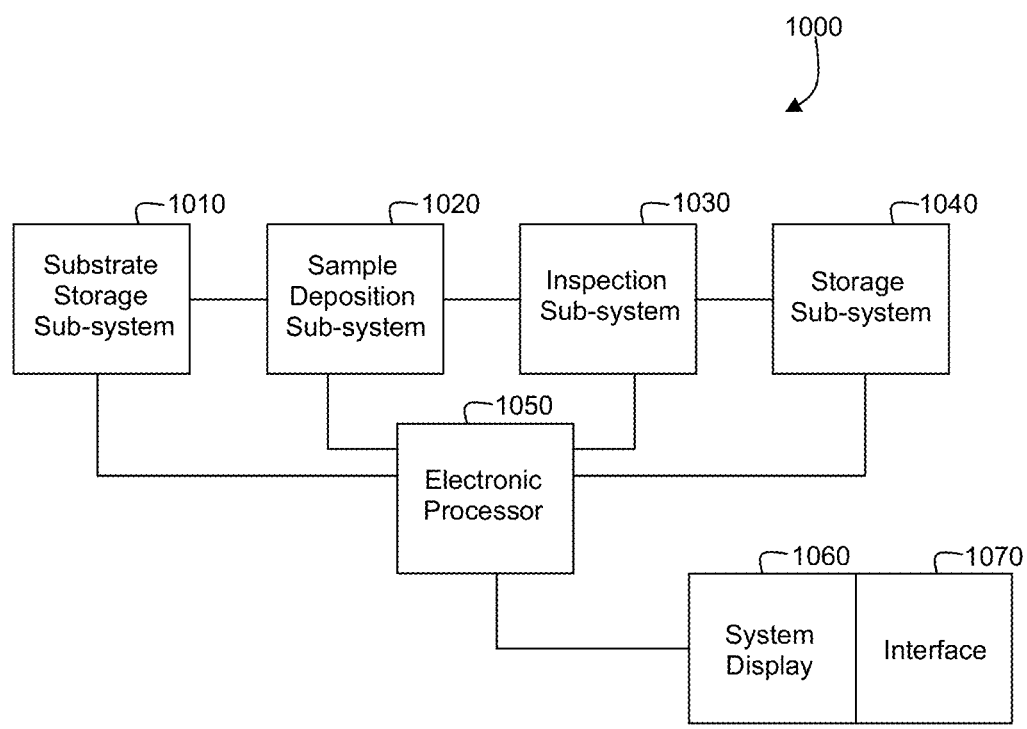
FIG. 10 is a schematic diagram of an automated sample processing system.

FIG. 10 shows a schematic diagram of an embodiment of an automated sample preparation system 1000. System 1000 includes multiple sub-systems for storing substrates, depositing samples on substrates, inspecting samples prepared on substrates, and storing prepared samples.

Substrate storage sub-system 1010 is configured to store substrates prior to the deposition of samples thereon. Substrates can include, for example, microscope slides, coverslips, and similar planar, optically transparent substrates. The substrates can be formed from a variety of different amorphous or crystalline materials including various types of glasses. Sub-system 1010 can include a manipulator that selects individual substrates from a storage container and transfers the selected substrates to sample deposition sub-system 1020.

Sample deposition sub-system 1020 deposits a selected quantity of a sample of interest—such as a blood sample—onto a substrate. Sub-system 1020 includes, in general, a variety of fluid transfer components (e.g., pumps, fluid tubes, valves) configured to deposit the sample. The fluid transfer components can also be configured to expose the substrate to solutions of various types, including wash solutions, one or more stains that bind to the sample, fixing solutions, and buffer solutions. Sub-system 1020 can also feature fluid removal components (e.g., a vacuum sub-system) and a drying apparatus to ensure that the sample is fixed to the substrate. A substrate manipulator can transfer the substrate supporting the sample to imaging sub-system 1030.

As discussed above, the methods and systems disclosed herein permit the determination of the thickness of substrate 102 based on images of the sample applicator that are reflected from lower surface 102*b* of the substrate. This thickness information can be used by sample deposition sub-system 1020. For example, as described in U.S. patent application Ser. No. 13/293,050 (incorporated by reference above), substrate thickness information can be used to determine how to orient the substrate in a specimen processing position, and the extent of agitation that occurs during the deposition process.

Inspection sub-system 1030 includes various components for obtaining images of samples on substrates, and for analyzing the images to determine information about the samples. For example, inspection sub-system 1030 can include one or more light sources (e.g., light emitting diodes, laser diodes, and/or lasers) for directing incident light to a sample. Imaging sub-system 1030 can also include an optical apparatus (e.g., a microscope objective) for capturing transmitted and/or reflected light from a sample. A detector (e.g., a CCD detector) coupled to the optical apparatus can be configured to capture images of the sample. Information derived from analysis of the images of the sample can be stored on a variety of optical and/or electronic storage media for later retrieval and/or further analysis.

Following inspection, a substrate manipulator can transfer the substrate to storage sub-system 1040. Storage sub-system 1040 can label individual substrates, for example, with information relating to the source of the sample applied to the substrate, the time of analysis, and/or any irregularities identified during analysis. Storage sub-system can also store processed substrates in multi-substrate racks, which can be removed from system 1000 as they are filled with substrates.

As shown in FIG. 10, each of the various sub-systems of system 1000 can be linked to a common electronic processor 1050 (which can be the same as electronic processor 162, or a different electronic processor). Processor 1050 can be configured to control the operation of each of the sub-systems of system 1000 in automated fashion, with relatively little (or no) input from a system operator. Results from the analysis of samples can be displayed on system display 1060 for a supervising operator. Interface 1070 permits the operator to issue commands to system 1000 and to manually review the automated analysis results.

Hardware and Software Implementation

The method steps and procedures described herein can be implemented in hardware or in software, or in a combination of both. In particular, an electronic processor (e.g., electronic processor 162) can include software and/or hardware instructions to perform any of the methods discussed above. The methods can be implemented in computer programs using standard programming techniques following the method steps and figures disclosed herein, and stored on a variety of non-transitory media such as magnetic disks, optical storage media such as compact discs and DVDs, solid state memory devices such as flash memory, and mechanical storage media such as hard disks. Program code is applied to input data to perform the functions described herein. The output information is applied to one or more output devices such as a printer, or a display device, or a web page on a computer monitor with access to a website, e.g., for remote monitoring.

Each program is preferably implemented in a high level procedural or object oriented programming language to communicate with a processor. However, the programs can be implemented in assembly or machine language, if desired. In any case, the language can be a compiled or interpreted language. Each computer program can be stored on a storage medium or device (e.g., an electronic memory) readable by the processor, for configuring and operating the processor to perform the procedures described herein.

Other Embodiments

A number of embodiments have been described. Nevertheless, it will be understood that various modifications may be made without departing from the spirit and scope of the disclosure. Accordingly, other embodiments are within the scope of the following claims.

What is claimed is:

1. A method for positioning a sample applicator relative to a substrate, the method comprising:
    obtaining an image of the sample applicator in proximity to the substrate, the image comprising a direct image region corresponding to the sample applicator and a first reflected image region corresponding to an image of the sample applicator reflected from a surface of the substrate;
    determining a position of an edge of the sample applicator in the direct image region;
    determining a position of a reflected edge of the sample applicator in the first reflected image region;
    determining a distance between the edge of the sample applicator and the reflected edge of the sample applicator; and
    determining the position of the sample applicator relative to the substrate based on the distance between the edges.

2. The method of claim 1, wherein obtaining the image of the sample applicator in proximity to the substrate comprises orienting a detector at an angle relative to the surface of the substrate, and recording the image using the detector.

3. The method of claim 1, wherein the position of the sample applicator relative to the substrate comprises a height of the sample applicator above the surface of the substrate.

4. The method of claim 3, wherein determining the height of the sample applicator above the surface of the substrate comprises calculating the height based on reference information that comprises correlation information relating the distance between the edge of the sample applicator and the reflected edge of the sample applicator to the height.

5. The method of claim 4, further comprising measuring a set of distances between the edge of the sample applicator and the reflected edge of the sample applicator, wherein measuring each member of the set of distances comprises:

translating the sample applicator to a new height above the surface of the substrate;

obtaining a second image of the sample applicator at the new height in proximity to the substrate, the second image comprising a direct image region corresponding to the sample applicator and a first reflected image region corresponding to an image of the sample applicator reflected from the surface of the substrate;

determining a position of an edge of the sample applicator in the direct image region of the second image;

determining a position of a reflected edge of the sample applicator in the first reflected image region of the second image; and determining a distance between the edge of the sample applicator in the direct image region and the reflected edge of the sample applicator in the first reflected image region of the second image.

6. The method of claim 5, further comprising determining a control setting associated with a target position of the sample applicator by interpolating between distances in the measured set of distances.

7. The method of claim 6, further comprising storing in a storage unit the control setting and information about a location of the sample applicator relative to the substrate.

8. The method of claim 7, further comprising:
translating the sample applicator in a direction perpendicular to a central axis of the applicator to a new location relative to the substrate;
measuring a set of distances between the edge of the sample applicator and the reflected edge of the sample applicator;
determining a control setting associated with a target position of the sample applicator at the new location; and
storing the control setting and information about the new location in the storage unit.

9. The method of claim 8, further comprising repeating the steps of translating the sample applicator in a direction perpendicular to the central axis of the sample applicator to a new location relative to the substrate, measuring a set of distances between the edge of the sample applicator and reflected edge of the sample applicator, determining a control setting associated with a target position of the sample applicator at the new location, and storing the control setting and information about the new location in the storage unit, until a number of locations about which information is stored is three or more.

10. The method of claim 9, wherein the number of locations about which information is stored is six or more.

11. The method of claim 9, further comprising determining coefficients of an equation of a surface of the substrate.

12. The method of claim 9, further comprising determining an orientation of the substrate relative to a plane perpendicular to the central axis of the sample applicator, wherein determining the orientation of the substrate comprises determining a slope of the substrate surface relative to the plane perpendicular to the central axis of the sample applicator.

13. The method of claim 5, wherein the set of distances comprises at least two distances.

14. The method of claim 5, wherein the set of distances comprises at least ten distances.

15. The method of claim 4, further comprising calibrating the correlation information, wherein calibrating the correlation information comprises:
determining an offset control signal value that causes an actuator of the sample applicator to provide an upward force that will just be overcome by the force of gravity;
storing the offset control signal value;
translating the sample applicator toward the substrate until a signal associated with a translation error of the actuator is within an error threshold; and
storing the position of the sample applicator when the signal associated with the translation error of the actuator is within the error threshold.

16. The method of claim 15, wherein calibrating the correlation information comprises setting the height of the sample applicator to zero at the stored position.

17. The method of claim 1, wherein determining a position of an edge of the sample applicator in the direct image region comprises:
selecting columns of pixels in the direct image region that extend in a direction parallel to a central axis of the sample applicator;
for each selected column, determining a position of maximum intensity change within the column;
determining the position of the edge of the sample applicator based on the positions of maximum intensity change in each selected column of pixels.

18. The method of claim 17, wherein determining the position of maximum intensity change within each selected column comprises:
for each pair of adjacent pixels in the selected column, determining a change in intensity;
determining a maximum intensity change between pairs of adjacent pixels in the selected column; and
fitting a functional form to the maximum intensity change between pairs of adjacent pixels to determine the position of maximum intensity change within the selected column.

19. The method of claim 17, wherein determining the position of the edge of the sample applicator comprises fitting the positions of maximum intensity change within each selected column to a functional form.

20. The method of claim 19, wherein determining the position of the edge of the sample applicator comprises determining an apex point of the sample applicator based on the fitted functional form.

21. The method of claim 1, wherein determining the position of the reflected edge of the sample applicator in the first reflected image region comprises:
selecting rows of pixels in the first reflected image region that extend in a direction perpendicular to an elongated axis of the sample applicator image;
for each selected row, determining an average of an m highest pixel intensities in the row, and determining an average of a k lowest pixel intensities in the row;
determining a contrast level associated with the row as a difference between the average of the m highest pixel intensities and the average of the k lowest pixel intensities; and
determining the position of the reflected edge of the sample applicator based on the contrast level in each selected row.

22. The method of claim 21, wherein determining the position of the reflected edge of the sample applicator based on the contrast level in each selected row comprises:
identifying a first portion of the first reflected image region based on a contrast level in each selected pixel row, wherein the first portion does not comprise the image of the sample applicator;
identifying a second portion of the first reflected image region based on a contrast level in each selected pixel row, wherein the second portion comprises the image of the sample applicator; and determining the position of the reflected edge of the sample applicator based on a difference in contrast levels between the first and second portions of the first reflected image region.

23. The method of claim 21, wherein m corresponds to at least one fifth of a total number of pixels in each selected row, k corresponds to at least one fifth of the total number of pixels in each selected row, and wherein no pixels in each selected row are common to the m pixels and the k pixels.

24. The method of claim 1, wherein the surface of the substrate is an upper surface of the substrate closest to the sample applicator.

25. The method of claim 24, wherein the image of the sample applicator in proximity to the substrate comprises a second reflected image region corresponding to an image of the sample applicator reflected from a lower surface of the substrate, the method further comprising:
    determining a position of a reflected edge of the sample applicator in the second reflected image region;
    determining a distance between the reflected edges of the sample applicator in the first and second reflected image regions; and
    determining a thickness of the substrate based on the distance between the reflected edges of the sample applicator in the first and second reflected image regions.

26. The method of claim 25, wherein determining the thickness of the substrate comprises calculating the thickness based on reference information that comprises correlation information relating the distance between the reflected edges of the sample applicator to the thickness.

27. The method of claim 25, wherein determining a position of a reflected edge of the sample applicator in the second reflected image region comprises:
    selecting rows of pixels in the second reflected image region that extend in a direction perpendicular to an elongated axis of the sample applicator image;
    for each selected row, determining an average of a p highest pixel intensities in the row, and determining an average of a q lowest pixel intensities in the row;
    determining a contrast level associated with the row as a difference between the average of the p highest pixel intensities and the average of the q lowest pixel intensities; and
    determining the position of the reflected edge of the sample applicator in the second reflected image region based on a difference between the contrast level in each selected pixel row in the second reflected image region and the contrast level in each selected pixel row in the first reflected image region.

28. The method of claim 27, wherein p corresponds to at least one fifth of a total number of pixels in each selected row, q corresponds to at least one fifth of the total number of pixels in each selected row, and wherein no pixels in each selected row are common to the p pixels and the q pixels.

29. A system, comprising:
    a sample applicator;
    a stage configured to support a substrate;
    a detector; and
    an electronic processor, wherein the system is configured so that when a substrate is supported by the stage:
        the detector is configured to obtain an image of the sample applicator in proximity to the substrate, the image comprising a direct image region corresponding to the sample applicator and a first reflected image region corresponding to an image of the sample applicator reflected from a surface of the substrate; and
        the electronic processor is configured to:
            determine a position of an edge of the sample applicator in the direct image region;
            determine a position of a reflected edge of the sample applicator in the first reflected image region;
            determine a distance between the edge of the sample applicator and the reflected edge of the sample applicator; and
            determine the position of the sample applicator relative to the substrate based on the distance between the edges.

30. The system of claim 29, wherein the position of the sample applicator relative to the substrate comprises a height of the sample applicator above the surface of the substrate, and wherein the electronic processor is configured to determine the height of the sample applicator based on reference information that comprises correlation information relating the distance between the edge of the sample applicator and the reflected edge of the sample applicator to the height.

31. The system of claim 30, wherein the electronic processor is configured to measure a set of distances between the edge of the sample applicator and the reflected edge of the sample applicator by:
    translating the sample applicator to a new height above the surface of the substrate;
    obtaining a second image of the sample applicator at the new height in proximity to the substrate, the second image comprising a direct image region corresponding to the sample applicator and a first reflected image region corresponding to an image of the sample applicator reflected from the surface of the substrate;
    determining a position of an edge of the sample applicator in the direct image region of the second image;
    determining a position of a reflected edge of the sample applicator in the first reflected image region of the second image; and
    determining a distance between the edge of the sample applicator in the direct image region and the reflected edge of the sample applicator in the first reflected image region of the second image.

32. The system of claim 31, wherein the electronic processor is configured to determine a control setting associated with a target position of the sample applicator by interpolating between distances in the measured set of distances.

33. The system of claim 32, further comprising a storage unit connected to the electronic processor, wherein the electronic processor is configured to store the control setting and information about a location of the sample applicator relative to the substrate in the storage unit.

34. The system of claim 33, wherein the electronic processor is further configured to:
    translate the sample applicator in a direction perpendicular to a central axis of the sample applicator to a new location relative to the substrate;
    measure a set of distances between the edge of the sample applicator and the reflected edge of the sample applicator;
    determine a control setting associated with the target position of the sample applicator at the new location; and
    store the control setting and information about the new location in the storage unit.

35. The system of claim 34, wherein the electronic processor is configured to determine coefficients of an equation of a plane corresponding to a surface of the substrate based on the stored control settings.

* * * * *